(12) United States Patent
Braun

(10) Patent No.: US 8,987,470 B2
(45) Date of Patent: Mar. 24, 2015

(54) PROCESS FOR THE PREPARATION OF PYRAZOLE-4-CARBOXAMIDES

(75) Inventor: Max Josef Braun, Wedemark (DE)

(73) Assignee: Solvay SA, Brussels (BE)

( * ) Notice: Subject to any disclaimer, the term of this patent is extended or adjusted under 35 U.S.C. 154(b) by 158 days.

(21) Appl. No.: 13/881,366

(22) PCT Filed: Oct. 25, 2011

(86) PCT No.: PCT/EP2011/068653
§ 371 (c)(1),
(2), (4) Date: Apr. 24, 2013

(87) PCT Pub. No.: WO2012/055864
PCT Pub. Date: May 3, 2012

(65) Prior Publication Data
US 2013/0225833 A1    Aug. 29, 2013

Related U.S. Application Data

(60) Provisional application No. 61/407,216, filed on Oct. 27, 2010.

(51) Int. Cl.
    *C07D 231/14*    (2006.01)

(52) U.S. Cl.
    CPC ................................. *C07D 231/14* (2013.01)
    USPC ..................................................... 548/374.1

(58) Field of Classification Search
    None
    See application file for complete search history.

(56) References Cited

U.S. PATENT DOCUMENTS

| | | | |
|---|---|---|---|
| 5,965,774 A | 10/1999 | Yoshikawa et al. | |
| 6,369,093 B1 | 4/2002 | Elbe et al. | |
| 2005/0119130 A1 | 6/2005 | Walter | |
| 2008/0015244 A1 | 1/2008 | Dunkel et al. | |
| 2008/0051446 A1 | 2/2008 | Ehrenfreund et al. | |
| 2008/0108686 A1 | 5/2008 | Gewehr et al. | |
| 2008/0153707 A1 | 6/2008 | Gewehr et al. | |
| 2008/0188442 A1 | 8/2008 | Lamberth et al. | |
| 2009/0069398 A1 | 3/2009 | Dunkel et al. | |
| 2009/0105325 A1 | 4/2009 | Furuya et al. | |
| 2009/0163569 A1 | 6/2009 | Tobler et al. | |
| 2010/0022782 A1 | 1/2010 | Zierke et al. | |

FOREIGN PATENT DOCUMENTS

| | | |
|---|---|---|
| EP | 0824099 A1 | 2/1998 |
| EP | 1161420 B1 | 5/2005 |
| EP | 1480955 B1 | 6/2007 |
| EP | 1992617 A1 | 11/2008 |
| EP | 1490342 B1 | 12/2010 |
| WO | WO 2004035589 A1 | 4/2004 |
| WO | WO 2005123690 A1 | 12/2005 |
| WO | WO 2006015865 A1 | 2/2006 |
| WO | WO 2006015866 A1 | 2/2006 |
| WO | WO 2006087343 A1 | 8/2006 |
| WO | WO 2007009717 A1 | 1/2007 |
| WO | WO 2007031323 A1 | 3/2007 |
| WO | WO 2008053991 A1 | 5/2008 |
| WO | WO 2009021987 A1 | 2/2009 |
| WO | WO 2009028280 A1 | 3/2009 |
| WO | WO 2009138375 A1 | 11/2009 |
| WO | WO 2012010692 A1 | 1/2012 |
| WO | WO 2012025469 A1 | 3/2012 |

OTHER PUBLICATIONS

U.S. Appl. No. 12/673,030, filed May 17, 2011, Max Josef Braun.
U.S. Appl. No. 13/810,626, filed Jan. 18, 2013, Max Josef Bruan, et al.
Fevig, John M., et al—"Synthesis and SAR of Benzamidine Factor Xa Inhibitors Containing a Vicinally-Substituted Heterocyclic Core" 2001, Bioorganic & Medicinal Chemistry Letters, vol. 11, Issue No. 5, Pergamon; pp. 641-645; 5 pgs.

*Primary Examiner* — Kamal Saeed

(57) ABSTRACT

A process for the manufacture of pyrazole-4-carboxamides, in particular, of 3-difluoromethyl-1-methyl-1H-pyrazole-4-carboxamides which are useful as pharmaceuticals and agrochemicals. The carboxamides are prepared from the corresponding pyzole-4-carboxylic acid esters and appropriate amine in the presence of a base. The reaction is performed in a reaction medium which is essentially free of water; alternatively, the base is used in an amount equal to or greater than 0.25 equivalents per mole of amine.

19 Claims, No Drawings

PROCESS FOR THE PREPARATION OF PYRAZOLE-4-CARBOXAMIDES

The present application is a U.S. national stage entry under 35 U.S.C. §371 of International Application No. PCT/EP2011/068653 filed Oct. 25, 2011, which claims the benefit of the U.S. provisional application No. 61/407,216 filed on Oct. 27, 2011, the whole content of this application being herein incorporated by reference.

The invention concerns a process for the manufacture of 1H-pyrazole-4-carboxamides, in particular 3-difluoromethyl-1-methyl-1H-pyrazole-4-carboxamides, which are useful as pharmaceuticals and agrochemicals.

Particular examples of 3-difluoromethyl-1-methyl-1H-pyrazole-4-carboxamides are for instance Bixafen, Sedaxane, Isopyrazam and Fluxapyraxad.

Bixafen having the chemical name N-(3',4'-dichloro-5-fluoro-[1,1'-biphenyl]-2-yl)-3-(difluoro-methyl)-1-methyl-1H-pyrazole-4-carboxamide (Cas Number 581809-46-3) and its manufacturing process is described in WO 03/070705.

Sedaxane is a mixture of isomers N-(2-[1,1'-bicyclopropyl]-2-ylphenyl)-3-(difluoromethyl)-1-methyl 1H-pyrazole-4-carboxamide (Cas Number 874967-67-6). Sedaxane and its manufacturing process are for example described in WO 2006/015865 and WO 2006/015866.

Isopyrazam is a mixture of isomers of 3-(difluoromethyl)-1-methyl-N-[1,2,3,4-tetrahydro-9-isopropyl-1,4-methanonaphthalen-5-yl]pyrazole-4-carboxamide (Cas Number 881685-58-1). Isopyrazam and its manufacturing process are described in WO 2004/035589.

Fluxapyroxad having the chemical name 3-(Difluoromethyl)-1-methyl-N-(3',4',5'-trifluorobiphenyl-2-yl)-1H-pyrazole-4-carboxamide and its manufacturing process is described in WO 2006/087343.

1H-pyrazole-4-carboxamides are generally obtained by reacting the corresponding 4-carboxylic acid pyrazole or the activated form of said carboxylic acid, for example an acid chloride, with an appropriate amine, see for example WO 03/070705 (EP1490342), WO 2005/123690, WO 2006/087343 or WO 2007/009717.

It is an object of the present invention to provide a process for the synthesis of 1H-pyrazole-4-carboxamides which allows, in particular, in an economically manner for high yield, high purity, and high efficiency for the manufacture of the target product. The process can have environmental benefits.

The invention consequently relates to a process for the manufacture of for the manufacture of compounds of formula (I)

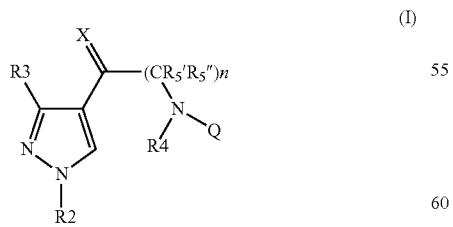

(I)

wherein
R2 is H or an organic residue
R3 is H, an alkyl group having from 1 to 12 carbon atoms, a halogenated alkyl group having from 1 to 12 carbon atoms, an aralkyl group, an aryl group, a halogen
R4 is H, an alkyl group having from 1 to 12 carbon atoms, a halogenated alkyl group having from 1 to 12 carbon atoms, an aralkyl group, an aryl group, a halogen
R5' and R5" are each independently selected from H, an alkyl group having from 1 to 12 carbon atoms, a halogenated alkyl group having from 1 to 12 carbon atoms, an aralkyl group, an aryl group, a halogen
n=0 to 10
X is oxygen or sulfur
Q is a group of any of formulae (Q1) to (Q38) herein below:

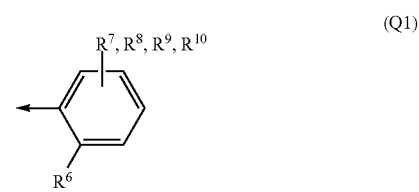
(Q1)

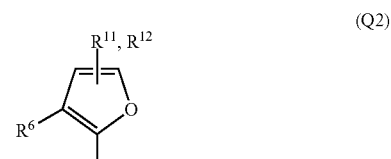
(Q2)

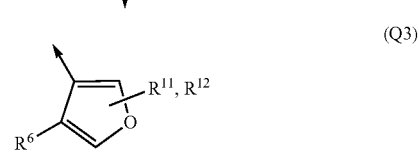
(Q3)

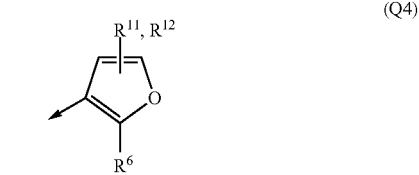
(Q4)

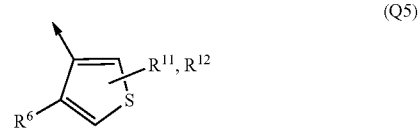
(Q5)

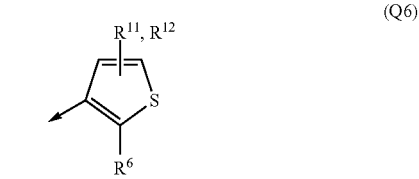
(Q6)

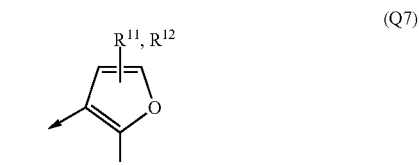
(Q7)

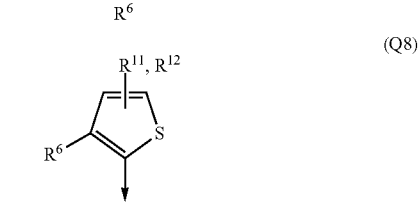
(Q8)

-continued
(Q9) 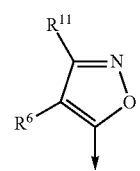
(Q10) 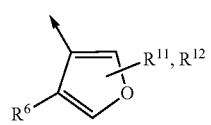
(Q11) 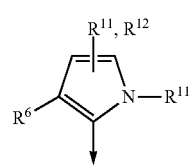
(Q12) 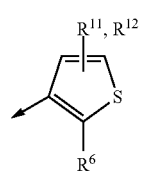
(Q13) 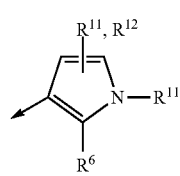
(Q14) 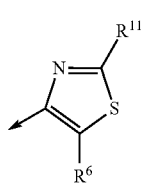
(Q15) 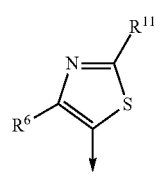
(Q16) 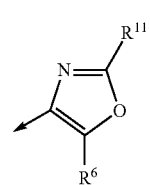
(Q17) 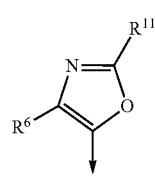
-continued
(Q18) 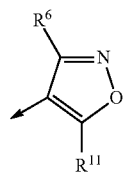
(Q19) 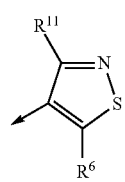
(Q20) 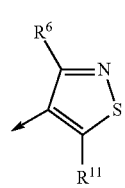
(Q21) 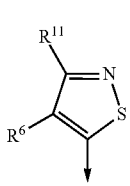
(Q22) 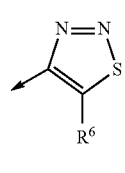
(Q23) 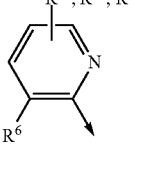
(Q24) 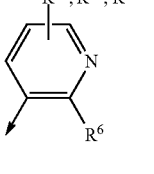
(Q25) 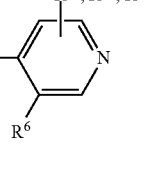
(Q26) 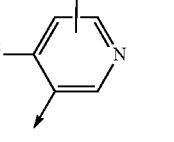

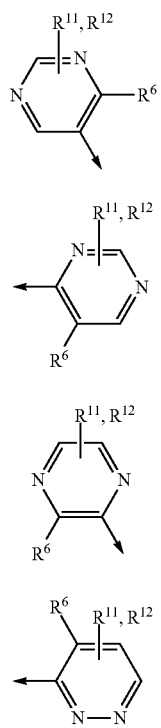
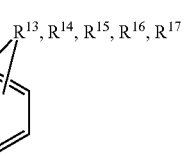
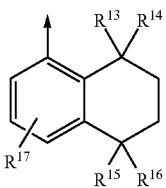
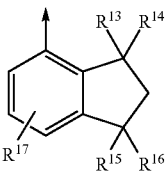
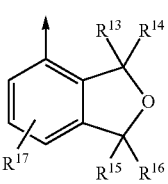
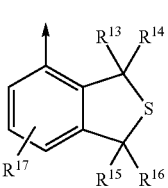
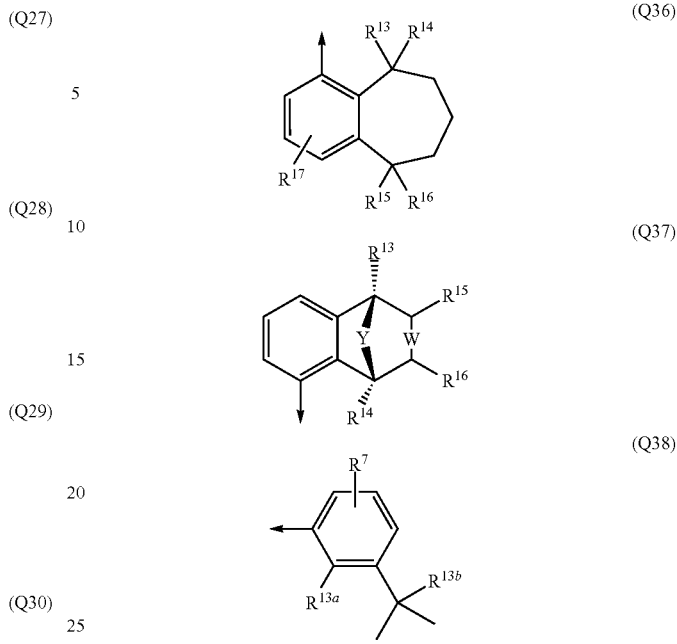

wherein $R^6$ is a hydrogen, $C_{1-12}$ alkyl, $C_{2-12}$ alkenyl or $C_{2-12}$ alkynyl group, which may be substituted by 1 to 6 substituents, each substituent independently selected from halogen, cyano, $C_{1-4}$ alkoxy, $C_{1-4}$ thioalkyl, COO—$C_{1-4}$ alkyl, =N—OH, =N-0-($C_{1-4}$ alkyl), $C_{3-8}$ cycloalkyl, which may itself be substituted by 1 to 3 substituents, each independently selected from $C_{1-4}$ alkyl, halogen, $C_{1-4}$ alkoxy and $C_{1-4}$ haloalkoxy, and $C_{4-8}$ cycloalkenyl, which may itself be substituted by 1 to 3 substituents, each independently selected from $C_{1-4}$ alkyl, halogen, $C_{1-4}$ alkoxy and $C_{1-4}$ haloalkoxy;

or $R^6$ is a $C_{3-8}$ cycloalkyl, $C_{4-8}$ cycloalkenyl or $C_{5-8}$ cycloalkadienyl group, which may be substituted by 1 to 3 substituents, each independently selected from halogen, $C_{1-4}$ alkyl, $C_{1-4}$ haloalkyl, $C_{1-4}$ alkoxy, $C_{1-4}$ haloalkoxy, $C_{1-4}$ thioalkyl, $C_{3-6}$ cycloalkyl, which may itself be substituted by 1 to 3 substituents, each independently selected from $C_{1-4}$ alkyl, halogen, $C_{1-4}$ alkoxy and $C_{1-4}$ haloalkoxy, and phenyl, which may itself be substituted by 1 to 5 independently selected halogen atoms;

or $R^6$ is a $C_{6-12}$ bicycloalkyl, $C_{6-12}$ bicycloalkenyl or $C_{6-12}$ bicycloalkadienyl group, which may be substituted by 1 to 3 substituents, each independently selected from halogen, $C_{1-4}$ alkyl and $C_{1-4}$ haloalkyl;

or $R^6$ is phenyl, which may be substituted by 1 to 3 substituents, each independently selected from halogen, cyano, nitro, $C_{1-4}$ alkyl, $C_{1-4}$ haloalkyl, $C_{1-4}$ alkoxy, $C_{1-4}$ alkylthio, $C_{1-4}$ haloalkoxy, $C_{1-4}$ haloalkylthio, C(H)=N—OH, C(H)=N—O($C_{1-6}$ alkyl), C($C_{1-6}$ alkyl)=N—OH, C($C_{1-6}$ alkyl)=N—O—($C_{1-6}$ alkyl), (Z)C≡CR, (Z)$_n$CR$^{28}$=CR$^{26}$R$^{27}$, phenyl, which may itself be substituted by 1 to 3 substituents, each independently selected from halogen, cyano, nitro, $C_{1-4}$ alkyl, $C_{1-4}$ haloalkyl, $C_{1-4}$ alkoxy, $C_{1-4}$ haloalkoxy, $C_{1-4}$ haloalkylthio, C(H)=N—OH, C(H)=N—O($C_{1-6}$ alkyl), C($C_{1-6}$ alkyl)=N—OH and C($C_{1-6}$ alkyl)=N—O—($C_{1-6}$ alkyl), and thienyl, which may itself be substituted by 1 to 3 substituents, each independently selected from halogen, cyano, nitro, $C_{1-4}$ alkyl, $C_{1-4}$ haloalkyl, $C_{1-4}$ alkoxy, $C_{1-4}$ haloalkoxy, $C_{1-4}$ haloalkylthio, C(H)=N—OH, C(H)=N—O($C_{1-6}$ alkyl), C($C_{1-6}$ alkyl)=N—OH and C($C_{1-6}$ alkyl)=N—O—($C_{1-6}$ alkyl);

or $R^6$ is a 5-6 membered heterocyclic ring, wherein the heterocyclic ring contains 1 to 3 heteroatoms, each heteroatom independently chosen from oxygen, sulphur and nitrogen, wherein the heterocyclic ring may be substituted 1 to 3 substituents, each independently selected from halogen, cyano, nitro, $C_{1-4}$ alkyl, $C_{1-4}$ haloalkyl, $C_{1-4}$ alkoxy, $C_{1-4}$ alkylthio, $C_{1-4}$alkylthio, $C_{1-4}$ haloalkoxy, $C(H)=N-O-(C_{1-6}$ alkyl) and $C(C_{1-6}$ alkyl)$=N-O-(C_{1-6}$ alkyl), $C_{2-5}$ alkenyl, $C_{2-5}$ alkynyl, CHO, $COOC_{1-6}$ alkyl, $CrC_4$ alkoxy-$C_1$-$C_4$ alkyl, $CrC_4$ haloalkoxy-$C_1$-$C_4$ alkyl, $(Z)_pC \equiv CR$, $(Z)_nCR^{28}=CR^{26}R^{27}$, phenyl, which may itself be substituted by 1 to 3 substituents, each independently selected from halogen, cyano, nitro, $C_{1-4}$ alkyl, $C_{1-4}$ haloalkyl, $C_{1-4}$ alkoxy, $C_{1-4}$ haloalkoxy, $C_{1-4}$ haloalkylthio, $C(H)=N-OH$, $C(H)=N-O(C_{1-6}$ alkyl), $C(C_{1-6}$ alkyl)$=N-OH$ and $C(C_{1-6}$ alkyl)$=N-O-(C_{1-6}$ alkyl), and thienyl, which may itself be substituted by 1 to 3 substituents, each independently selected from halogen, cyano, nitro, $C_{1-4}$ alkyl, $C_{1-4}$ haloalkyl, $C_{1-4}$ alkoxy, $C_{1-4}$ haloalkoxy, $C_{1-4}$ haloalkylthio, $C(H)=N-OH$, $C(H)=N-O(C_{1-6}$ alkyl), $C(C_{1-6}$ alkyl)$=N-OH$ and $C(C_{1-6}$ alkyl)$=N-O-(C_{1-6}$ alkyl), and wherein two substituents on adjacent carbon atoms of the 5-6 membered heterocyclic ring together may form a group $-CR^{6a}=CR^{6a}=CR^{6a}-CR^{6a}-$, wherein each $R^{6a}$ independently is selected from hydrogen, halogen, cyano, nitro, $C_{1-4}$ alkyl, $C_{1-4}$ haloalkyl, $C_{1-4}$ alkoxy, $C_{1-4}$ haloalkoxy, $C_{1-4}$ haloalkylthio, $C(H)=N-OH$, $C(H)=N-O(C_{1-6}$ alkyl), $C(C_{1-6}$ alkyl)$=N-OH$ and $C(C_{1-6}$ alkyl)$=N-O-(C_{1-6}$ alkyl);

or $R^6$ is an aliphatic saturated or unsaturated group containing 3 to 13 carbon atoms and at least one silicon atom, wherein the aliphatic group may contain 1 to 3 heteroatoms, each heteroatom independently selected from oxygen, nitrogen and sulphur, and wherein the aliphatic group may be substituted by 1 to 4 independently selected halogen atoms;

or $R^6$ is $(CR^aR^b)_m$-Cy-$(CR^cR^d)_n-Y_1$;

or $R^6$ is $C_{1-6}$ alkoxy, $C_{1-6}$ haloalkoxy, $C_{2-6}$ alkenyloxy, $C_{2-6}$ haloalkenyloxy, $C_{2-6}$ alkinyloxy, $C_{3-6}$ cycloalkyloxy, $C_{1-4}$ alkyl-$C_{3-7}$ cycloalkyloxy, $C_{5-7}$ cycloalkenyloxy or $C_{1-4}$ alkyl-$C_{5-7}$ cycloalkenyloxy;

Z is $C_{1-4}$ alkylene;

p is 0 or 1;

$R^{25}$ is hydrogen, halogen, $C_{1-4}$ alkyl, $C_{1-4}$ haloalkyl, $C_{1-4}$ alkoxy ($C_{1-4}$) alkyl, $C_{1-4}$ haloalkoxy ($C_{1-4}$) alkyl or $Si(C_{1-4}$ alkyl)$_3$;

$R^{26}$ and $R^{27}$ are each, independently, hydrogen, halogen, $C_{1-4}$ alkyl or $C_{1-4}$ haloalkyl;

$R^{28}$ is hydrogen, $C_{1-4}$ alkyl or $C_{1-4}$ haloalkyl;

$R^a$, $R^b$, $R^c$ and $R^d$ are each, independently, hydrogen or a $C_{1-4}$ alkyl group, which may substituted by 1 to 6 substituents, each substituent independently selected from halogen, hydroxy, cyano, carboxyl, methoxycarbonyl, ethoxycarbonyl, methoxy, ethoxy, methylsulfonyl, ethylsulfonyl, difluoromethoxy, trifluoromethoxy, trifluoromethylthio and trifluorothiomethoxy;

Cy is a carbocyclic or heterocyclic 3-7 membered ring, which may be saturated, unsaturated or aromatic and which may contain a silicon atom as a ring member, wherein $(CR^aR^b)_m$ and $(CR^cR^d)_n$ may be bound either to the same carbon or silicon atom of Cy or to different atoms separated by 1, 2 or 3 ring members, wherein the carbocyclic or heterocyclic 3-7 membered ring may substituted by 1 to 6 substituents, each substituent independently selected from halogen, $C_{1-4}$ alkyl, $C_{2-4}$ alkenyl, $C_{1-4}$ haloalkyl, $C_{1-4}$alkoxy and halo-$C_{1-4}$ alkoxy;

$Y_1$ is $Si(O_{p1}Z^1)(O_qZ^2)(O \leq Z^3)$ and provided that Cy contains a silicon atom as a ring member then $Y_1$ may also be hydrogen;

$Z^1$ and $Z^2$ are independently methyl or ethyl;

$Z^3$ is a $C_{1-4}$ alkyl or a $C_{2-4}$ alkenyl group, which may be interrupted by one heteroatom selected from O, S and N, and wherein the $C_{1-4}$ alkyl or $C_{2-4}$ alkenyl group may be substituted by 1 to 3 independently selected halogen atoms;

m and n are each independently 0, 1, 2 or 3;

$p_1$, q and s are each independently 0 or 1;

$R^7$, $R^8$, $R^9$, $R^{10}$, $R^{11}$, $R^{12}$ and $R^{12a}$ are each, independently, hydrogen, halogen, cyano, nitro, $C_{1-4}$ alkyl, $C_{1-4}$ haloalkyl, $C_{1-4}$ alkoxy, $C_{1-4}$ haloalkoxy, $C_{1-4}$ thioalkyl or $C_{1-4}$ thiohaloalkyl;

$R^{13}$, $R^{14}$, $R^{15}$, $R^{16}$ and $R^{17}$ are each, independently, hydrogen, halogen, cyano, nitro, $C_{1-4}$ alkyl, $C(O)CH_3$, $C_{1-4}$ haloalkyl, $C_{1-4}$ alkoxy, $C_{1-4}$ haloalkoxy, $C_{1-4}$ thioalkyl, $C_{1-4}$ thiohaloalkyl, hydroxymethyl or $C_{1-4}$ alkoxymethyl;

W is a single or a double bond; and

Y is O, $N(R^{18})$, S or $(CR^{19}R^{20})(CR^{21}R^{22})_{m1}(CR^{23}R^{24})_{n1}$;

$R^{18}$ is hydrogen, $C_{1-4}$ alkyl, formyl, $C_{1-4}$ alkoxy($C_{1-4}$)alkyl, $C(=O)C_{1-4}$ alkyl, which may be substituted by halogen or $C_{1-4}$-alkoxy, or $C(=O)O-C_{1-6}$ alkyl, which may be substituted by halogen, $C_{1-4}$ alkoxy or CN;

$R^{19}$, $R^{20}$, $R^{21}$, $R^{22}$, $R^{23}$ and $R^{24}$ are each independently hydrogen, halogen, hydroxy, $C_{1-4}$ alkoxy, $C_{1-6}$ alkyl, which may be substituted by 1 to 3 substituents selected from halogen, hydroxy, =O, $C_{1-4}$ alkoxy, O—C(O)—$C_{1-4}$ alkyl, phenyl, naphthyl, anthracyl, fluorenyl, indanyl or a 3-7 membered carbocyclic ring (which itself may be substituted by 1 to 3 methyl groups), $C_{1-6}$ alkenyl, which may be substituted by 1 to 3 substituents selected from halogen, hydroxy, =O, $C_{1-4}$ alkoxy, O—C(O)—$C_{1-4}$ alkyl, phenyl, naphthyl, anthracyl, fluorenyl, indanyl or a 3-7 membered carbocyclic ring (which itself may be substituted by 1 to 3 methyl groups), or a 3-7 membered carbocyclic ring, which may contain 1 heteroatom selected from nitrogen and oxygen, and wherein the 3-7 membered carbocyclic ring may be substituted by 1 to 3 methyl groups;

or $R^{19}$, $R^{20}$ together with the carbon atom to which they are attached form a carbonyl-group, a 3-5 membered carbocyclic ring, which may be substituted by 1 to 3 methyl groups, $C_{1-6}$ alkylidene, which may be substituted by 1 to 3 methyl groups, or $C_{3-6}$ cycloalkylidene, which may be substituted by 1 to 3 methyl groups;

$m_1$ is 0 or 1;

$n_1$ is 0 or 1;

$R^{13a}$ is a $C_1$-$C_4$ alkyl, $C_2$-$C_4$ alkenyl or $C_2$-$C_4$ alkynyl group, which may be substituted by 1 to 6 substituents, each substituent independently selected from halogen, hydroxy, cyano, $C_{1-4}$ alkoxycarbonyl, formyl, nitro, $C_1$-$C_4$ alkoxy, $C_1$-$C_4$ haloalkoxy, $C_1$-$C_4$ alkylthio, $C_1$-$C_4$ haloalkylthio, $HC(OR^{29})=N-$ and $R^{30}R^{31}NN=C(H)-$;

$R^{29}$, $R^{30}$ and $R^{31}$ independently of one another are hydrogen or $C_1$-$C_4$ alkyl;

$R^{13b}$ is a $C_1$-$C_6$ alkyl group, which may be substituted by 1 to 6 substituents, each substituent independently selected from halogen, hydroxy, cyano, $C_{1-4}$ alkoxycarbonyl, formyl, nitro, $C_1$-$C_4$ alkoxy, $C_1$-$C_4$ haloalkoxy, $C_1$-$C_4$ alkylthio, $C_1$-$C_4$ haloalkylthio, $HC(OR^{32})=N-$ and $R^{33}R^{34}NN=C(H)-$;

$R^{32}$, $R^{33}$ and $R^{24}$ independently of one another are hydrogen or $C_1$-$C_4$ alkyl;

$R^{13c}$ is hydrogen or halogen; and tautomers/isomers/enantiomers of these compounds which comprises reacting a compound of formula (II)

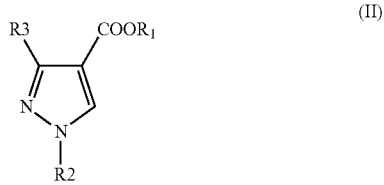

wherein:
R1 is an organic residue
R2 and R3 are as defined above, with an amine of formula (III): QNHR4 (III) wherein Q is as defined above, in the presence of a base.

In a first embodiment of the process according to the present invention, the process is carried out in a reaction medium which is essentially free of water.

Specifically, it has been found, surprisingly, that when a compound of formula (II) and an amine of formula (III) are reacted in the presence of a base in a reaction medium that is essentially free of water, a highly efficient production of the desired carboxamide of formula (I) was obtained.

The reaction medium generally contains not more than 3100 mg/kg of water. The reaction medium often contains not more than 1000 mg/kg of water. A reaction medium containing not more than 800 mg/kg of water is suitable for use. The reaction medium preferably contains not more than 100 mg/kg of water. A reaction medium containing not more than 100 mg/kg of water is most particularly preferred. Needless to say, the process can be carried out in a totally anhydrous reaction medium. However, it has been found that the presence of traces of water in small amounts is not harmful. Typically, the process according to the invention is carried out with a reaction medium containing more than 10 mg/kg of water, or even more than 50 mg/kg of water.

The water content of the reaction medium can be controlled, for example, by removing the traces of water from the reactor used. It is possible, for example, prior to introducing the reaction medium, to heat the reactor and/or to purge it with a dry gas. Furthermore, the water content in the constituents of the reaction medium can be reduced, for example in the compound of formula (II), the amine of formula (III) and the base, and optionally in the solvent. Operations which can be used to reduce the water content in the constituents of the reaction medium are, for example, a drying operation such as, for example, an adsorption on a solid adsorbent or a distillation operation.

In a second embodiment of the process according to the present invention, the process is carried out in such a way that the base is used in an amount equal to or greater than 0.25 equivalents, per mol amine of formula (III). Preferably this amount is equal to or greater than 0.5 equivalents, more preferably equal to or greater than 1.0 equivalents, most preferably equal to or greater than 1.5 equivalents, per mol amine of formula (III).

It has been found that controlling the amount of the base in the reaction medium improves the efficiency of the process and the yield and purity of the desired carboxamide of formula (I).

The invention will be further described in more detail and the definitions and preferences described below for the compounds including starting compounds and target compounds and process conditions related to the process according to the invention equally apply to the first and second embodiment, indicated above and further embodiments, described below, of the process according to the invention.

The term "organic residue" is intended to denote in particular linear or branched alkyl or alkylene groups which may contain hetero atoms, such as in particular boron, silicon, nitrogen, oxygen or sulphur atoms and halogen atoms, cycloalkyl groups, heterocycles and aromatic systems. The organic residue may contain double or triple bonds and functional groups.

The organic residue comprises at least 1 carbon atom. It often comprises at least 2 carbon atoms. It preferably comprises at least 3 carbon atoms. More particularly preferably, it comprises at least 5 carbon atoms.

The organic residue generally comprises at most 100 carbon atoms. It often comprises at most 50 carbon atoms. It preferably comprises at most 40 carbon atoms. More particularly preferably, it comprises at most 30 carbon atoms.

R1 is typically selected from the group consisting of H, linear or branched alkyl or alkylene groups, cycloalkyl or cycloalkylene groups, heterocycles and aromatic systems, optionally containing heteroatoms, double bonds, triple bonds, functional groups and mixtures thereof.

R2 is usually selected from the group consisting of H, linear or branched alkyl or alkylene groups, cycloalkyl or cycloalkylene groups, heterocycles and aromatic systems, optionally containing heteroatoms, double bonds, triple bonds, functional groups and mixtures thereof.

The term "alkyl group" is intended to denote in particular a linear or branched alkyl substituent comprising from 1 to 20 carbon atoms, preferably 1, 2, 3, 4, 5, 6, 7, 8, 9 or 10 carbon atoms. Specific examples of such substituents are methyl, ethyl, n-propyl, isopropyl, n-butyl, isobutyl, tert-butyl, n-pentyl, isopentyl, n-hexyl, 2-hexyl, n-heptyl, n-octyl and benzyl.

The term "cycloalkyl group" is intended to denote in particular a substituent comprising at least one saturated carbocycle containing 3 to 10 carbon atoms, preferably 5, 6 or 7 carbon atoms. Specific examples of such substituents are cyclopropyl, cyclobutyl, cyclopentyl, cyclohexyl and cycloheptyl.

The term "alkylene group" or "cycloalkylene group" is intended to denote in particular the divalent radicals derived from the alkyl or cycloalkyl groups as defined above.

When the organic residue contains one or optionally more double bonds, it is often chosen from an alkenyl or cycloalkenyl group comprising from 2 to 20 carbon atoms, preferably 2, 3, 4, 5, 6, 7, 8, 9 or 10 carbon atoms. Specific examples of such groups are vinyl, 1-allyl, 2-allyl, n-but-2-enyl, isobutenyl, 1,3-butadienyl, cyclopentenyl, cyclohexenyl and styryl.

When the organic residue contains one or optionally more triple bonds, it is often chosen from an alkinyl group comprising from 2 to 20 carbon atoms, preferably 2, 3, 4, 5, 6, 7, 8, 9 or 10 carbon atoms. Specific examples of such groups are ethinyl, 1-propinyl, 2-propinyl, n-but-2-inyl and 2-phenylethinyl.

When the organic residue contains one or optionally more aromatic systems, it is often an aryl group comprising from 6 to 24 carbon atoms, preferably from 6 to 12 carbon atoms. Specific examples of such groups are phenyl, 1-tolyl, 2-tolyl, 3-tolyl, xylyl, 1-naphthyl and 2-naphthyl.

The term "heterocycle" is intended to denote in particular a cyclic system comprising at least one saturated or unsaturated ring made up of 3, 4, 5, 6, 7 or 8 atoms, at least one of which is a hetero atom. The hetero atom is often chosen from B, N, O, Si, P and S. It is more often chosen from N, O and S.

Specific examples of such heterocycles are aziridine, azetidine, pyrrolidine, piperidine, morpholine, 1,2,3,4-tetrahydroquinoline, 1,2,3,4-tetrahydroisoquinoline, perhydroquinoline, perhydroisoquinoline, isoxazolidine, pyrazoline, imidazoline, thiazoline, tetrahydrofuran, tetrahydrothiophene, pyran, tetrahydropyran and dioxane.

The organic residues as defined above may be unsubstituted or substituted with functional groups. The term "functional group" is intended to denote in particular a substituent comprising or consisting of a hetero atom. The hetero atom is often chosen from B, N, O, Al, Si, P, S, Sn, As and Se and the halogens. It is more often chosen from N, O, S and P, in particular N, O and S.

The functional group generally comprises 1, 2, 3, 4, 5 or 6 atoms.

By way of functional groups, mention may, for example, be made of halogens, a hydroxyl group, an alkoxy group, a mercapto group, an amino group, a nitro group, a carbonyl group, an acyl group, an optionally esterified carboxyl group, a carboxamide group, a urea group, a urethane group and the thiol derivatives of the abovementioned groups containing a carbonyl group, phosphine, phosphonate or phosphate groups, a sulphoxide group, a sulphone group and a sulphonate group.

The term "halogenated alkyl group" is intended to denote in particular an alkyl group comprising from 1 to 20 carbon atoms and at least one halogen, preferably 1, 2, 3, 4, 5, 6, 7, 8, 9 or 10 carbon atoms and at least one halogen. Suitable halogenated alkyl groups are selected for example from chlorinated alkyl groups such as chloromethyl, dichloromethyl, trichloromethyl, 1-chloroethyl or 2,2,2-trichloroethyl fluorinated alkyl groups such as fluoromethyl, difluoromethyl, trifluoromethyl, 1-fluoroethyl, 2-fluoroethyl, 2,2-difluoroethyl, 2,2,2-trifluoroethyl or pentafluoroethyl, chlorofluorinated alkyl groups such as chlorofluoromethyl, dichlorofluoromethyl, chlorodifluoromethyl, 2-chloro-2-fluoroethyl, 2-chloro-2,2-difluoroethyl or 2,2-dichloro-2-fluoroethyl, brominated alkyl groups such as bromomethyl and 1-bromoethyl.

In a preferred embodiment of the process according to the invention, R1 is $C_1$-$C_8$-alkyl, $C_1$-$C_8$-haloalkyl, $C_3$-$C_8$-cycloalkyl, $C_1$-$C_4$-alkoxy-$C_1$-$C_4$-alkyl, $C_3$-$C_8$-cycloalkoxy-$C_1$-$C_4$-alkyl, $C_2$-$C_8$-alkenyl or is benzyl which is optionally substituted by 1, 2 or 3 substituents $R^{Y1}$ independently of one another selected from the group consisting of $C_1$-$C_4$-alkyl, $C_1$-$C_4$-alkoxy and nitro; and R2 is hydrogen, $C_1$-$C_4$-alkyl, benzyl or phenyl, where the two last-mentioned substituents may be unsubstituted or optionally substituted by 1, 2 or 3 substituents $R^{Y2}$ independently of one another selected from the group consisting of halogen, nitrile, nitro, $C_1$-$C_4$-alkyl, $C_1$-$C_4$-haloalkyl, $C_1$-$C_4$-alkoxy and $C_1$-$C_4$-haloalkoxy; and R3 is an alkyl group or a halogenated alkyl group. $R_4$ is hydrogen, $C_1$-$C_8$-alkyl, benzyl or phenyl.

The terms, used in the definition of the variables, for organic groups, such as, for example, the term "halogen", are collective terms representing the individual members of these groups of organic moieties.

The prefix $C_x$-$C_y$ denotes the number of possible carbon atoms in the case in question. $C_1$-$C_4$-Alkyl includes, for example, methyl, ethyl, propyl, 1-methylethyl, butyl, 1-methylpropyl, 2-methylpropyl or 1,1-dimethylethyl.

The term "halogen" denotes in each case fluorine, bromine, chlorine or iodine, especially fluorine, chlorine or bromine. This also applies, correspondingly, to halogen in combination with other meanings, such as haloalkyl or haloalkoxy.

The term "alkoxy" is, for example, methoxy, ethoxy, propoxy, i-propoxy, n-butoxy, isobutoxy, sec-butoxy and tert-butoxy; preferably methoxy and ethoxy.

Haloalkoxy is, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy and 2,2,2-trichloroethoxy; preferably difluoromethoxy, 2-chloroethoxy and trifluoromethoxy. Alkylthio is, for example, methylthio, ethylthio, propylthio, isopropylthio, n-butylthio, isobutylthio, sec-butylthio or tert-butylthio, preferably methylthio and ethylthio.

The term "$C_1$-$C_4$-alkoxy-$C_1$-$C_4$-alkyl", as used herein, describes $C_1$-$C_4$-alkyl radicals where one carbon atom is attached to a $C_1$-$C_4$-alkoxy radical. Examples of these are $CH_2$—$OCH_3$, $CH_2$—$OC_2H_5$, n-propoxymethyl, $CH_2$—OCH($CH_3$)$_2$, n-butoxymethyl, (1-methylpropoxy)methyl, (2-methylpropoxy)methyl, $CH_2$—OC($CH_3$)$_3$, 2-(methoxy)ethyl, 2-(ethoxy)ethyl, 2-(n-propoxy)ethyl, 2-(1-methylethoxy)ethyl, 2-(n-butoxy)ethyl, 2-(1-methylpropoxy)ethyl, 2-(2-methylpropoxy)ethyl, 2-(1,1-dimethylethoxy)ethyl, 2-(methoxy)propyl, 2-(ethoxy)propyl, 2-(n-propoxy)propyl, 2-(1-methylethoxy)propyl, 2-(n-butoxy)propyl, 2-(1-methylpropoxy)propyl, 2-(2-methylpropoxy)propyl, 2-(1,1-dimethylethoxy)propyl, 3-(methoxy)propyl, 3-(ethoxy)propyl, 3-(n-propoxy)propyl, 3-(1-methylethoxy)propyl, 3-(n-butoxy)propyl, 3-(1-methylpropoxy)propyl, 3-(2-methylpropoxy)propyl, 3-(1,1-dimethylethoxy)propyl, 2-(methoxy)butyl, 2-(ethoxy)butyl, 2-(n-propoxy)butyl, 2-(1-methylethoxy)butyl, 2-(n-butoxy)butyl, 2-(1-methylpropoxy)butyl, 2-(2-methylpropoxy)butyl, 2-(1,1-dimethylethoxy)butyl, 3-(methoxy)butyl, 3-(ethoxy)butyl, 3-(n-propoxy)butyl, 3-(1-methylethoxy)butyl, 3-(n-butoxy)butyl, 3-(1-methylpropoxy)butyl, 3-(2-methylpropoxy)butyl, 3-(1,1-dimethylethoxy)butyl, 4-(methoxy)butyl, 4-(ethoxy)butyl, 4-(n-propoxy)butyl, 4-(1-methylethoxy)butyl, 4-(n-butoxy)butyl, 4-(1-methylpropoxy)butyl, 4-(2-methylpropoxy)butyl, 4-(1,1-dimethylethoxy)butyl.

The term "$C_2$-$C_8$-alkenyl", as used herein, describes straight-chain and branched unsaturated hydrocarbon radicals having 2 to 8 carbon atoms and at least one carbon-carbon double bond, such as, for example, ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl, 1-heptenyl, 2-heptenyl, 1-octenyl or 2-octenyl.

In a preferred embodiment of the process according to the invention, X is oxygen, R1 is $C_1$-$C_4$-alkyl, $C_1$-$C_4$-haloalkyl or benzyl, in particular methyl, ethyl, trifluoroethyl, pentafluoropropyl, hexafluoro-iso-propyl, n-propyl or isopropyl; R1 is especially ethyl; and R2 is H or $C_1$-$C_4$-alkyl; R2 is especially methyl; R3 is selected from a group consisting of fluoromethyl, difluoromethyl, trifluoromethyl, chlorofluoromethyl, dichlorofluoromethyl, and chlorodifluoromethyl; R3 is especially difluoromethyl. R4 is selected from the group consisting of hydrogen and $C_1$-$C_4$-alkyl; R4 is especially hydrogen; Q is Q1 or Q37.

In one embodiment, Q is Q1 and $R^6$ is a hydrogen, $C_{1-12}$ alkyl, $C_{2-12}$ alkenyl or $C_{2-12}$ alkynyl group, which may be substituted by 1 to 6 substituents, each substituent independently selected from halogen, cyano, $C_{1-4}$ alkoxy, $C_{1-4}$ thioalkyl, COO—$C_{1-4}$ alkyl, =N—OH, =N-0-($C_{1-4}$ alkyl), $C_{3-8}$ cycloalkyl, which may itself be substituted by 1 to 3 substituents, each independently selected from $C_{1-4}$ alkyl, halogen, $C_{1-4}$ alkoxy and $C_{1-4}$ haloalkoxy, and $C_{4-8}$ cycloalkenyl, which may itself be substituted by 1 to 3 substituents, each independently selected from $C_{1-4}$ alkyl, halogen, $C_{1-4}$ alkoxy and $C_{1-4}$ haloalkoxy, $R^6$ is especially a hydrogen; $R^7$, $R^8$, $R^9$ and $R^{10}$ are each, independently, hydrogen, halogen, $C_{1-4}$ alkyl, $C_{1-4}$ haloalkyl, $C_{1-4}$ alkoxy, $C_{1-4}$ haloalkoxy, $R^7$, $R^8$, $R^9$ and $R^{10}$ are especially each, independently, hydrogen and halogen, said halogen is especially chlorine or fluorine.

In another embodiment, Q is Q1 and $R^6$ is phenyl, which may be substituted by 1 to 3 substituents, each independently selected from halogen, cyano, nitro, $C_{1-4}$ alkyl, $C_{1-4}$ haloalkyl, $C_{1-4}$ alkoxy, $C_{1-4}$ alkylthio, $C_{1-4}$ haloalkoxy, $C_{1-4}$ haloalkylthio, C(H)=N—OH, C(H)=N—O($C_{1-6}$ alkyl), C($C_{1-6}$ alkyl)=N—OH, C($C_{1-6}$ alkyl)=N—O—($C_{1-6}$ alkyl), (Z)C=CR, (Z)$_n$CR$^{28}$=CR$^{26}$R$^{27}$, phenyl, which may itself be substituted by 1 to 3 substituents, each independently selected from halogen, cyano, nitro, $C_{1-4}$ alkyl, $C_{1-4}$ haloalkyl, $C_{1-4}$ alkoxy, $C_{1-4}$ haloalkoxy, $C_{1-4}$ haloalkylthio, C(H)=N—OH, C(H)=N—O($C_{1-6}$ alkyl), C($C_{1-6}$ alkyl)=N—OH and C($C_{1-6}$ alkyl)=N—O—($C_{1-6}$ alkyl), and thienyl, which may itself be substituted by 1 to 3 substituents, each independently selected from halogen, cyano, nitro, $C_{1-4}$ alkyl, $C_{1-4}$ haloalkyl, $C_{1-4}$ alkoxy, $C_{1-4}$ haloalkoxy, $C_{1-4}$ haloalkylthio, C(H)=N—OH, C(H)=N—O($C_{1-6}$ alkyl), C($C_{1-6}$ alkyl)=N—OH and C($C_{1-6}$ alkyl)=N—O—($C_{1-6}$ alkyl); $R^6$ is especially phenyl, which is substituted in the para-position by halogen, wherein said phenyl may be further substituted by 1 to 2 substituents, each independently selected from halogen, $C_{1-4}$ alkyl and $C_{1-4}$ haloalkyl; $R^7$, $R^8$, $R^9$ and $R^{10}$ are especially each, independently, hydrogen and halogen, said halogen is especially chlorine or fluorine.

In another embodiment, Q is Q1 and $R^6$ is a $C_{3-8}$ cycloalkyl, $C_{4-8}$ cycloalkenyl or $C_{5-8}$ cycloalkadienyl group, which may be substituted by 1 to 3 substituents, each independently selected from halogen, $C_{1-4}$alkyl, $C_{1-4}$ haloalkyl, $C_{1-4}$ alkoxy, $C_{1-4}$ haloalkoxy, $C_{1-4}$ thioalkyl, $C_{3-6}$ cycloalkyl, which may itself be substituted by 1 to 3 substituents, each independently selected from $C_{1-4}$ alkyl, halogen, $C_{1-4}$ alkoxy and $C_{1-4}$ haloalkoxy, and phenyl, which may itself be substituted by 1 to 5 independently selected halogen atoms; $R^6$ is especially a $C_{3-8}$ cycloalkyl, which may be substituted by 1 to 3 substituents, each independently selected from halogen, $C_{1-4}$alkyl, $C_{1-4}$ haloalkyl.

In another embodiment, Q is Q37 and $R^{13}$, $R^{14}$, $R^{15}$ and $R^{16}$ are each, independently, hydrogen, halogen, $C_{1-4}$ alkyl, C(O)CH$_3$, $C_{1-4}$ haloalkyl, $C_{1-4}$ alkoxy; in particular $R^{14}$, $R^{15}$ and $R^{16}$ are each, independently, hydrogen, methyl, methoxy or C(O)CH$_3$; $R^{13}$, $R^{14}$, $R^{15}$ and $R^{16}$ are especially each, independently, hydrogen or methyl and W is a single bound; and Y is O or (CR$^{19}$R$^{20}$)(CR$^{21}$R$^{22}$)$_{m1}$(CR$^{23}$R$^{24}$)$_{n1}$; preferably Y is (CR$^{19}$R$^{20}$)(CR$^{21}$R$^{22}$)$_{m1}$(CR$^{23}$R$^{24}$)$_{n1}$, more preferably Y is (CR$^{19}$R$^{20}$)(CR$^{21}$R$^{22}$)$_{m1}$ and $R^{19}$, $R^{20}$, $R^{21}$, $R^{22}$, $R^{23}$ and $R^{24}$ are each independently hydrogen, halogen, $C_{1-4}$ alkoxy, $C_{1-6}$ alkyl, which may be substituted by 1 to 3 substituents selected from halogen, hydroxy, =O, $C_{1-4}$ alkoxy, O—C(O)—$C_{1-4}$ alkyl, phenyl, naphthyl, anthracyl, fluorenyl, indanyl or a 3-7 membered carbocyclic ring (which itself may be substituted by 1 to 3 methyl groups), $C_{1-6}$ alkenyl, which may be substituted by 1 to 3 substituents selected from halogen, hydroxy, =O, $C_{1-4}$ alkoxy, O—C(O)—$C_{1-4}$ alkyl, phenyl, naphthyl, anthracyl, fluorenyl, indanyl or a 3-7 membered carbocyclic ring (which itself may be substituted by 1 to 3 methyl groups), or a 3-7 membered carbocyclic ring, which may contain 1 heteroatom selected from nitrogen and oxygen, and wherein the 3-7 membered carbocyclic ring may be substituted by 1 to 3 methyl groups; or $R^{19}$, $R^{20}$ together with the carbon atom to which they are attached form a carbonyl-group, a 3-5 membered carbocyclic ring, which may be substituted by 1 to 3 methyl groups, $C_{1-6}$ alkylidene, which may be substituted by 1 to 3 methyl groups, or $C_{3-6}$ cycloalkylidene, which may be substituted by 1 to 3 methyl groups; especially $R^{19}$ and $R^{20}$ together with the carbon atom to which they are attached form a 3-membered or 5-membered carbocyclic ring; preferably $R^{21}$, $R^{22}$, $R^{23}$ and $R^{24}$ are each independently hydrogen or CH$_3$.

In a first specific preferred embodiment, Q is a group of formula Q39

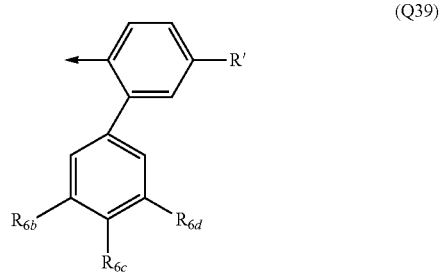

(Q39)

wherein R', $R_{6b}$, $R_{6c}$ and $R_{6d}$ are each, independently, hydrogen or halogen, said halogen is especially chlorine or fluorine.

In a second specific preferred embodiment, Q is a group of formula Q40

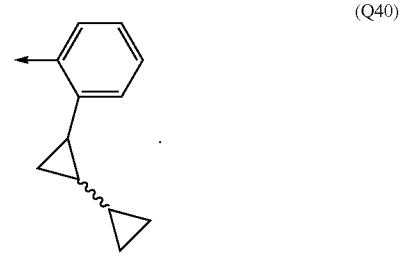

(Q40)

In a third specific preferred embodiment, Q is a group of formula Q41

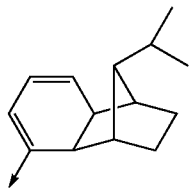

(Q41)

In a particularly preferred aspect of the process of the present invention, an amine of formula (III): QNHR4 (III) wherein Q is selected from a group consisting of Q35 to Q41, is reacted with ethyl 1-methyl-3-difluoromethyl-pyrazole-4-carboxylate (DFMMP).

Amines of the formula (III) are either known, for example, from EP 1490342, EP 0824099, EP 1480955 (B1), WO 2004/035589, WO 2007/031323, or they can be prepared according to generally known methods.

The formation of the compound of formula (II) can be carried out, for example, analogously to the reaction described in the patent applications EP-10170633.1 and EP-10173899.5. The respective content of said patent applications is incorporated by reference into the present patent application.

In the process according to the invention, the reaction is generally carried out in an inert solvent. Examples of suitable inert solvents include hydrocarbons such as benzene, toluene, xylene or cyclohexane; halogenated hydrocarbons such as dichloromethane, trichloromethane or tetrachloromethane; halogenated aromatic hydrocarbons such as chlorobenzene, straight chain or cyclic ethers such as diethyl ether, ethylene glycol dimethyl ether, diethylene glycol dimethyl ether, tetrahydrofuran or dioxane, nitriles such as acetonitrile or propionitrile, amides such as N,N-dimethylformamide, diethylformamide or N-methylpyrrolidinone; these inert solvents can be used alone or in combination as a mixture.

In a preferred specific embodiment, the solvent is selected from the group consisting of halogenated hydrocarbons such as dichloromethane, trichloromethane or tetrachloromethane; and straight chain or cyclic ethers such as diethyl ether, ethylene glycol dimethyl ether, diethylene glycol dimethyl ether, tetrahydrofuran or dioxane. In a further specific embodiment, the solvent is different than chlorobenzene, more particularly different than a halogenated aromatic hydrocarbon.

The reaction is preferably carried out in a straight chain or cyclic ether, in particular in a cyclic ether and particularly preferable in tetrahydrofuran (THF).

In a preferred aspect of the process of the present invention, the solvent is substantially free of water.

For the purpose of the present invention, the term "solvent substantially free of water" denotes in particular that the content of water in the solvent is equal to or lower than 3100 mg/kg of water, preferably equal to or lower than 500 mg/kg of water, more preferably equal to or lower than 400 mg/kg of water, most preferably equal to or lower than 50 mg/kg of water. The solvent can be completely anhydrous. However, the solvent substantially free of water generally contains at least 5 mg/kg of water, often at least 25 mg/kg of water. Solvents which are substantially free of water allow shorter residence time and/or lower temperatures thereby leading to a more economical and environmental beneficial process.

If appropriate, the solvent is used usually in an amount of from 50 to 99 by weight, preferably from 60 to 99% by weight, more preferably from 75 to 99% by weight of the solvent relative to the total weight of the reaction medium.

In the process according to the invention, the base is preferably a non-nucleophilic base.

It has been found that a non-nucleophilic base advantageously increases the nucleophilicity of the amine of formula (III) while the reaction of the base with the esters of formula (II) is substantially minimized or absent. Consequently, the use of a base allows increasing the reaction rate and efficiency of the process.

For the purpose of the present invention, the term "non-nucleophilic base" denotes a base which is at the same time a poor nucleophile.

Examples of suitable non-nucleophilic bases include sterically hindered alcoholates, such as potassium tert-butoxide (KOtBu), sodium tert-butoxide (NaOtBu); amines such as DBU (1,8-diazabicyclo[5.4.0]undec-7-ene), DBN (1,5-Diazabicyclo[4.3.0]non-5-ene), TMG (tetramethylguanidine), TBD (triazabicyclodecene); lithium compounds such as lithium diisopropylamide (LDA), tert-Butyllithium (tBuLi), lithium tetramethylpiperidide (Li-TMP); silicium compounds such as Sodium hexamethyldisilazane (Na-HMDS), Potassium hexamethyldisilazane (K-HMDS). Aluminium compounds such trimethyl aluminium. From among those, potassium tert-butoxide, trimethyl aluminium LDA, and DBU are more preferred. Most preferred base is potassium tert-butoxide.

If desired, the base maybe an environmental friendly base which is for example prepared via a ring opening reaction of β or γ-lactones.

The process according to the invention is, if appropriate, carried out in the presence of a suitable phase transfer catalyst such as for example a crown ether. This allows to increase the yield and to reduce the reaction time.

If desired, the solvent can be chosen on account of respective pKa of base and reagents.

In the process according to the invention, the temperature of the reaction is generally at least 0° C. The temperature of the reaction is often at least 15° C. Preferably, this temperature is at least 25° C. The temperature of the reaction is generally at most the boiling temperature of the solvent. Typically, the temperature of the reaction is equal to or lower than 120° C., particularly equal to or lower than 100° C., more particularly equal to or lower than 90° C., most particularly equal to or lower than 70° C., a temperature equal to or lower than 50° C. being especially suitable. A temperature from 15 to 70° C. is suitable, a temperature from 15 to 50° C. is particularly preferred, a temperature of 25° C. is very particularly preferred.

Should the disclosure of any patents, patent applications, and publications which are incorporated herein by reference conflict with the description of the present application to the extent that it may render a term unclear, the present description shall take precedence.

The following example is intended to further explain the invention without limiting it.

In these examples and throughout this specification the abbreviations employed are defined as follows: DFMMP is ethyl 1-methyl-3-difluoromethyl-pyrazole-4-carboxylate, MeOH is methanol, PPTs is pyridinium p-toluenesulfonate, DCM is dichloromethane, THF is tetrahydrofurane, DMAP is 4-dimethylaminopyridine, DMF is N,N-dimethylformamide.

EXAMPLE 1

Synthesis of 1H-Pyrazole-4-Carboxamides in the Presence of a Base and an Inert Solvent Starting from Anilines 1a-1d and Ethyl 1-methyl-3-difluoromethyl-pyrazole-4-carboxylate (DFMMP) According to Following Scheme

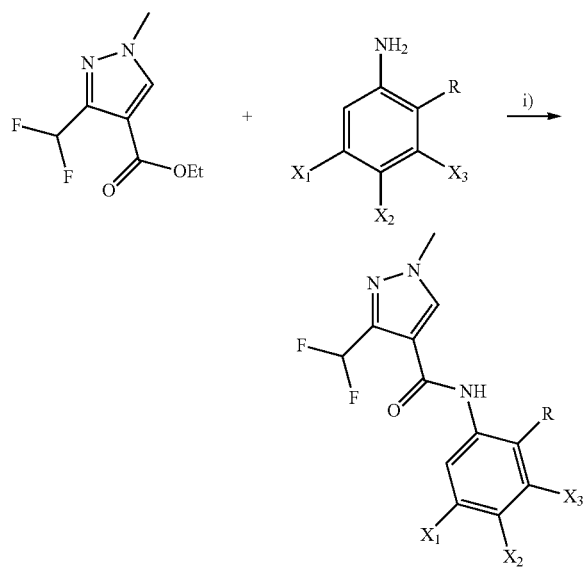

Aniline 1a: R = Ph, $X_{1,2,3}$ = H; Aniline 1b: R = H, $X_{1,3}$ = H, $X_2$ = F;
Aniline 1c: R = $CH_3$, $X_{1,3}$ = H, $X_2$ = F and Aniline 1d: R = H, $X_{1,2,3}$ = Cl General Procedure in Order to Test Optimal Reaction Conditions:

The aniline compound (1a to 1d) (1 eq.) and DFMMP (1 eq.), both dissolved in an inert solvent were added to a suspension of a base (1.5 eq.) in the inert solvent at 0° C. The conversion of aniline to anilide was followed by GC analyses. The experimental data and results are summarized in the Table below:

| Aniline | Reagent | Conditions | Result |
| --- | --- | --- | --- |
| 1a | No reagent | Thermal (up to 200° C.) | Decomposition |
| 1a | No reagent | Thermal (up to 150° C.) | No product formation |
| 1a | MeOH | Reflux | No conversion |
| 1a | NaOMe, Toluol | Reflux | No conversion |
| 1a | Trifluorethanol | Reflux | No conversion |
| 1a | Toluol, PPTs | Reflux | No conversion |
| 1a | Xylol, PPTs | Reflux | No conversion |
| 1a | Trimethylaluminium, DCM | RT | Good conversion |
| 1a | DMF | 150° C. | No product formation |
| 1a | DMF, cat. DMAP | 90° C. | No product formation |
| 1a | DMF, cat. KOtBu | 90° C. | Traces of product |
| 1a | KOtBu, THF | RT | Complete conversion |
| 1b | NaOMe, Toluol | Reflux | No conversion |
| 1b | Trimethylaluminium, DCM | RT | Good conversion |
| 1b | KOtBu, THF | RT | Complete conversion |
| 1c | KOtBu, THF | RT | Complete conversion |
| 1d | KOtBu, THF | RT | Good conversion, but not so "clean reaction" |

EXAMPLE 2

Synthesis of Fluxapyroxad®

1.37 g 3',4',5'-trifluorobiphenyl-2-amine (1 eq.; 6.1 mmol) in 5 ml THF and 1.25 g (6.1 mmol) DFMMP in 5 ml THF were added to a suspension of 1.03 g (1.5 eq.; 9.2 mmol) KOtBu in 15 ml THF at 0° C. After stirring at room temperature over night the reaction mixture was poured out in water and extracted twice with acetic ether. The purified organic extracts were washed with water and saturated NaCl solution, dried, filtered and concentrated over sodium sulphate. The residue was filtered through a silicagel column (SiO2; hexane/acetic ether 1:1); and the desired product 3-(difluoromethyl)-1-methyl-N-(3',4',5'-trifluorobiphenyl-2-yl)-1H-pyrazole-4-carboxamide was obtained with 70% purity (1.8 g).

EXAMPLE 3

Synthesis of Bixafen®

2.1 g 3',4'-Dichlor-5-fluorobiphenyl-2-amine (1 eq.; 8.2 mmol) in 5 ml THF and 1.67 g DFMMP (8.2 mmol; 1 eq) in 5 ml THF were added to a suspension of 1.38 g (1.5 eq.; 12.3 mmol) KOtBu in 20 ml THF at 0° C. After stirring at room temperature over night the reaction mixture was poured out in water and extracted twice with acetic ether. The purified organic extracts were washed with water and a saturated NaCl solution, dried, filtered and concentrated over sodium sulphate. The residue was filtered through a silicagel column ($SiO_2$; hexane/acetic ether 1:1) and the desired product N-(3',4'-dichloro-5-fluorobiphenyl-2-yl)-3-(difluoromethyl)-1-methyl-1H-pyrazole-4-carboxamide was obtained in 60% yield (2.03 g) (purity GC 100%; HPLC–254 nm=94.6%).

EXAMPLE 4

Synthesis of Isopyrazam®

1,2,3,4-tetrahydro-9-isopropyl-1,4-methanonaphthalen-5-amine 320 mg (1 eq.; 9:1 syn:anti mixture) in 2 ml THF and 325 mg (1.6 mmol) DFMMP (1) in 2 ml THF were added to a suspension of 268 mg (1.5 eq.) KOtBu in 10 ml THF at 0° C. After stirring at room temperature over night the reaction mixture was poured out in water and extracted twice with acetic ether. The purified organic extracts were washed with water and a saturated NaCl solution, dried, filtered and concentrated over sodium sulphate. The residue was filtrated through a silicagel column ($SiO_2$; hexane/acetic ether 1:1) and the desired product Isopyrazam® was obtained in 77% yield (440 mg) (purity GC 100%; HPLC–254 nm>99% as 86.5:12.7 syn:anti mixture).

EXAMPLE 5

Synthesis of Sedaxane®

The appropriate amine (1 eq) in 5 ml THF and DFMMP (1 eq) in 5 ml THF is added to a suspension of 1.5 eq. KOtBu in 20 ml THF at 0° C. After stirring at room temperature over night, the reaction mixture is poured out in water and extracted twice with acetic ether. The purified organic extracts are washed with water and a saturated NaCl solution, dried, filtered and concentrated over sodium sulphate. The residue is filtered through a silicagel column ($SiO_2$; hexane/acetic ether 1:1) and the desired product Sedaxane® is obtained.

The invention claimed is:

1. A process for the manufacture of compounds of formula (I)

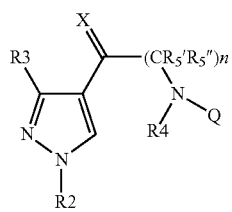
(I)

wherein
- R2 is H or an organic residue;
- R3 is H, an alkyl group having from 1 to 12 carbon atoms, a halogenated alkyl group having from 1 to 12 carbon atoms, an aralkyl group, an aryl group, or a halogen;
- R4 is H, an alkyl group having from 1 to 12 carbon atoms, a halogenated alkyl group having from 1 to 12 carbon atoms, an aralkyl group, an aryl group, or a halogen;
- R5' and R5" are each independently selected from the group consisting of H, an alkyl group having from 1 to 12 carbon atoms, a halogenated alkyl group having from 1 to 12 carbon atoms, an aralkyl group, an aryl group, and a halogen;
- n=0 to 10;
- X is oxygen or sulfur;
- Q is a group selected from the group consisting of formulae (Q1) to (Q38):

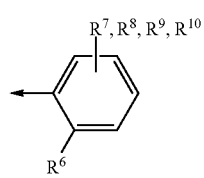
(Q1)

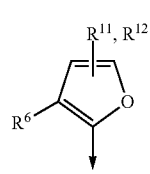
(Q2)

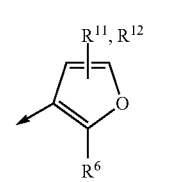
(Q3)

(Q4)

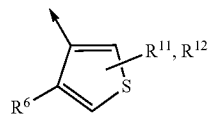
(Q5)

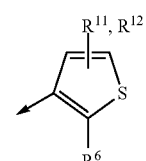
(Q6)

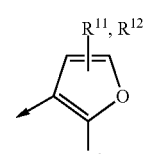
(Q7)

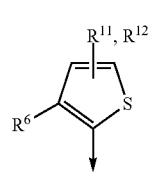
(Q8)

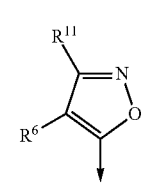
(Q9)

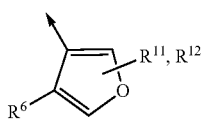
(Q10)

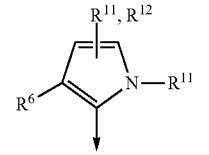
(Q11)

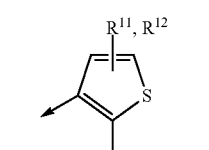
(Q12)

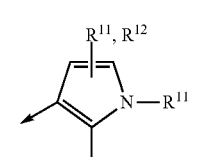
(Q13)

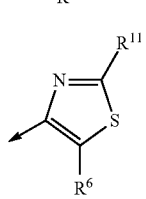
(Q14)

-continued
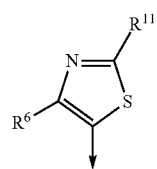 (Q15)
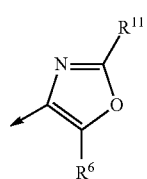 (Q16)
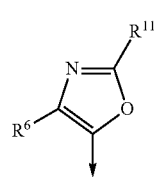 (Q17)
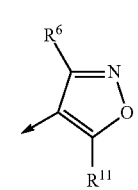 (Q18)
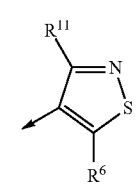 (Q19)
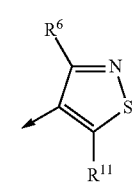 (Q20)
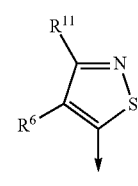 (Q21)
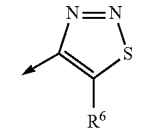 (Q22)
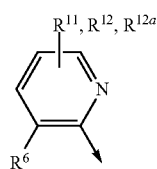 (Q23)
-continued
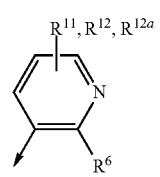 (Q24)
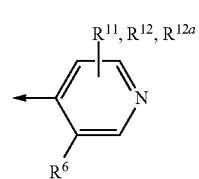 (Q25)
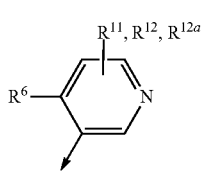 (Q26)
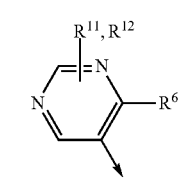 (Q27)
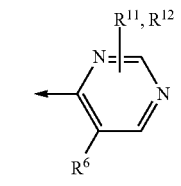 (Q28)
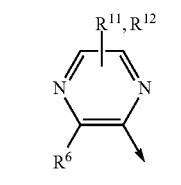 (Q29)
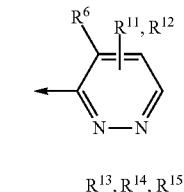 (Q30)
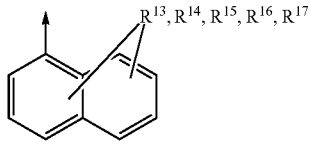 (Q31)
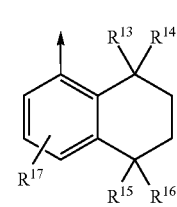 (Q32)

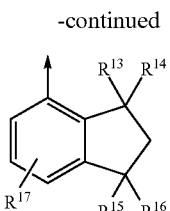
(Q33)

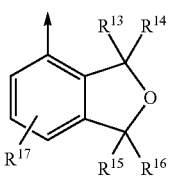
(Q34)

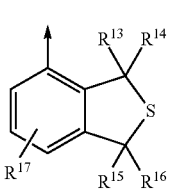
(Q35)

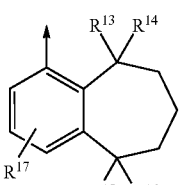
(Q36)

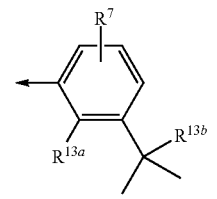
(Q37)

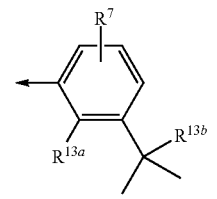
(Q38)

wherein:

$R^6$ is a hydrogen, $C_{1-12}$ alkyl, $C_{2-12}$ alkenyl, or $C_{2-12}$ alkynyl group, which may be substituted by 1 to 6 substituents, each substituent independently selected from the group consisting of halogen, cyano, $C_{1-4}$ alkoxy, $C_{1-4}$ thioalkyl, COO—$C_{1-4}$ alkyl, =N—OH, =N-0-($C_{1-4}$ alkyl), $C_{3-8}$ cycloalkyl, which may itself be substituted by 1 to 3 substituents, each independently selected from the group consisting of $C_{1-4}$ alkyl, halogen, $C_{1-4}$ alkoxy, $C_{1-4}$ haloalkoxy, and $C_{4-8}$ cycloalkenyl, which may itself be substituted by 1 to 3 substituents, each independently selected from the group consisting of $C_{1-4}$ alkyl, halogen, $C_{1-4}$ alkoxy, and $C_{1-4}$ haloalkoxy;

or $R^6$ is a $C_{3-8}$ cycloalkyl, $C_{4-8}$ cycloalkenyl or $C_{5-8}$ cycloalkadienyl group, which may be substituted by 1 to 3 substituents, each independently selected from the group consisting of halogen, $C_{1-4}$ alkyl, $C_{1-4}$ haloalkyl, $C_{1-4}$ alkoxy, $C_{1-4}$ haloalkoxy, $C_{1-4}$ thioalkyl, $C_{3-6}$ cycloalkyl, which may itself be substituted by 1 to 3 substituents, each independently selected from the group consisting of $C_{1-4}$ alkyl, halogen, $C_{1-4}$ alkoxy, and $C_{1-4}$ haloalkoxy, and phenyl, which may itself be substituted by 1 to 5 independently selected halogen atoms;

or $R^6$ is a $C_{6-12}$ bicycloalkyl, $C_{6-12}$ bicycloalkenyl, or $C_{6-12}$ bicycloalkadienyl group, which may be substituted by 1 to 3 substituents, each independently selected from the group consisting of halogen, $C_{1-4}$ alkyl, and $C_{1-4}$ haloalkyl;

or $R^6$ is phenyl, which may be substituted by 1 to 3 substituents, each independently selected from the group consisting of halogen, cyano, nitro, $C_{1-4}$ alkyl, $C_{1-4}$ haloalkyl, $C_{1-4}$ alkoxy, $C_{1-4}$ alkylthio, $C_{1-4}$ haloalkoxy, $C_{1-4}$ haloalkylthio, C(H)=N—OH, C(H)=N—O($C_{1-6}$ alkyl), C($C_{1-6}$ alkyl)=N—OH, C($C_{1-6}$ alkyl)=N—O—($C_{1-6}$ alkyl), (Z)C≡CR, $(Z)_nCR^{28}$=$CR^{26}R^{27}$, phenyl, which may itself be substituted by 1 to 3 substituents, each independently selected from the group consisting of halogen, cyano, nitro, $C_{1-4}$ alkyl, $C_{1-4}$ haloalkyl, $C_{1-4}$ alkoxy, $C_{1-4}$ haloalkoxy, $C_{1-4}$ haloalkylthio, C(H)=N—OH, C(H)=N—O($C_{1-6}$ alkyl), C($C_{1-6}$ alkyl)=N—OH, and C($C_{1-6}$ alkyl)=N—O—($C_{1-6}$ alkyl), and thienyl, which may itself be substituted by 1 to 3 substituents, each independently selected from the group consisting of halogen, cyano, nitro, $C_{1-4}$ alkyl, $C_{1-4}$ haloalkyl, $C_{1-4}$ alkoxy, $C_{1-4}$ haloalkoxy, $C_{1-4}$ haloalkylthio, C(H)=N—OH, C(H)=N—O($C_{1-6}$ alkyl), C($C_{1-6}$ alkyl)=N—OH, and C($C_{1-6}$ alkyl)=N—O($C_{1-6}$ alkyl);

or $R^6$ is a 5-6 membered heterocyclic ring, wherein the heterocyclic ring contains 1 to 3 heteroatoms, each heteroatom independently selected from the group consisting of oxygen, sulphur and nitrogen, wherein the heterocyclic ring may be substituted by 1 to 3 substituents, each independently selected from the group consisting of halogen, cyano, nitro, $C_{1-4}$ alkyl, $C_{1-4}$ haloalkyl, $C_{1-4}$ alkoxy, $C_{1-4}$ alkylthio, $C_{1-4}$ alkylthio, $C_{1-4}$ haloalkoxy, C(H)=N—O—($C_{1-6}$ alkyl), C($C_{1-6}$ alkyl)=N—O—($C_{1-6}$ alkyl), $C_{2-5}$ alkenyl, $C_{2-5}$ alkynyl, CHO, COOC$_1$-$C_6$ alkyl, $C_1$-$C_4$ alkoxy-$C_1$-$C_4$ alkyl, $C_1$-$C_4$ haloalkoxy-$C_1$-$C_4$ alkyl, $(Z)_pC$≡CR, $(Z)_nCR^{28}$=$CR^{26}R^{27}$, phenyl, which may itself be substituted by 1 to 3 substituents, each independently selected from the group consisting of halogen, cyano, nitro, $C_{1-4}$alkyl, $C_{1-4}$ haloalkyl, $C_{1-4}$ alkoxy, $C_{1-4}$ haloalkoxy, $C_{1-4}$ haloalkylthio, C(H)=N—OH, C(H)=N—O($C_{1-6}$ alkyl), C($C_{1-6}$ alkyl)=N—OH, and C($C_{1-6}$ alkyl)=N—O—($C_{1-6}$ alkyl), and thienyl, which may itself be substituted by 1 to 3 substituents, each independently selected from the group consisting of halogen, cyano, nitro, $C_{1-4}$ alkyl, $C_{1-4}$ haloalkyl, $C_{1-4}$ alkoxy, $C_{1-4}$ haloalkoxy, $C_{1-4}$ haloalkylthio, C(H)=N—OH, C(H)=N—O($C_{1-6}$ alkyl), C($C_{1-6}$ alkyl)=N—OR, and C($C_{1-6}$ alkyl)=N—O—($C_{1-6}$ alkyl), and wherein two substituents on adjacent carbon atoms of the 5-6 membered heterocyclic ring together may form a group —$CR^{6a}$—$CR^{6a}$=$CR^{6a}$—$CR^{6a}$—, wherein each $R^{6a}$ independently is selected from the group consisting of hydrogen, halogen, cyano, nitro, $C_{1-4}$ alkyl, $C_{1-4}$ haloalkyl, $C_{1-4}$ alkoxy, $C_{1-4}$ haloalkoxy, $C_{1-4}$ haloalkylthio, C(H)=N—OH, C(H)=N—O($C_{1-6}$ alkyl), C($C_{1-6}$ alkyl)=N—OH, and C($C_{1-6}$ alkyl)=N—O—($C_{1-6}$ alkyl);

or $R^6$ is an aliphatic saturated or unsaturated group containing 3 to 13 carbon atoms and at least one silicon atom, wherein the aliphatic group may contain 1 to 3 heteroatoms, each heteroatom independently selected from the group consisting of oxygen, nitrogen, and sulphur, and wherein the aliphatic group may be substituted by 1 to 4 independently selected halogen atoms;

or $R^6$ is $(CR^aR^b)_m$-Cy-$(CR^cR^d)_n$—$Y_1$;

or $R^6$ is $C_{1-6}$ alkoxy, $C_{1-6}$ haloalkoxy, $C_{2-6}$ alkenyloxy, $C_{2-6}$ haloalkenyloxy, $C_{2-6}$ alkenyloxy, $C_{3-6}$ cycloalkyloxy, $C_{1-4}$ alkyl-$C_{3-7}$ cycloalkyloxy, $C_{5-7}$ cycloalkenyloxy, or $C_{1-4}$ alkyl-$C_{5-7}$ cycloalkenyloxy;

Z is $C_{1-4}$ alkylene;

p is 0 or 1;

$R^{25}$ is hydrogen, halogen, $C_{1-4}$ alkyl, $C_{1-4}$ haloalkyl, $C_{1-4}$ alkoxy($C_{1-4}$)alkyl, $C_{1-4}$ haloalkoxy ($C_{1-4}$) alkyl, or Si($C_{1-4}$ alkyl)$_3$;

$R^{26}$ and $R^{27}$ are each, independently, hydrogen, halogen, $C_{1-4}$ alkyl, or $C_{1-4}$ haloalkyl;

$R^{25}$ is hydrogen, $C_{1-4}$ alkyl, or $C_{1-4}$ haloalkyl;

$R^a$, $R^b$, $R^c$ and $R^d$ are each, independently, hydrogen or a $C_{1-4}$ alkyl group, which may be substituted by 1 to 6 substituents, each substituent independently selected from the group consisting of halogen, hydroxy, cyano, carboxyl, methoxycarbonyl, ethoxycarbonyl, methoxy, ethoxy, methylsulfonyl, ethylsulfonyl, difluoromethoxy, trifluoromethoxy, trifluoromethylthio, and trifluorothiomethoxy;

Cy is a carbocyclic or heterocyclic 3-7 membered ring, which may be saturated, unsaturated or aromatic and which may contain a silicon atom as a ring member, wherein $(CR^aR^b)_m$ and $(CR^cR^d)_n$ may be bound either to the same carbon or silicon atom of Cy or to different atoms separated by 1, 2 or 3 ring members, wherein the carbocyclic or heterocyclic 3-7 membered ring may substituted by 1 to 6 substituents, each substituent independently selected from the group consisting of halogen, $C_{1-4}$ alkyl, $C_{2-4}$ alkenyl, $C_{1-4}$ haloalkyl, $C_{1-4}$ alkoxy, and halo-$C_{1-4}$ alkoxy;

$Y_1$ is Si($O_{p1}Z^1$)($O_qZ^2$)($O\leq X^3$) and provided that Cy contains a silicon atom as a ring member then $Y_1$ may also be hydrogen;

$Z^1$ and $Z^2$ are independently methyl or ethyl;

$Z^3$ is a $C_{1-4}$ alkyl or a $C_{2-4}$ alkenyl group, which may be interrupted by one heteroatom selected from the group consisting of O, S and N, and wherein the $C_{1-4}$ alkyl or $C_{2-4}$ alkenyl group may be substituted by 1 to 3 independently selected halogen atoms;

m and n are each independently 0, 1, 2, or 3;

$p_1$, q and s are each independently 0 or 1;

$R^7$, $R^8$, $R^9$, $R^{10}$, $R^{11}$, $R^{12}$ and $R^{12a}$ are each, independently, hydrogen, halogen, cyano, nitro, $C_{1-4}$ alkyl, $C_{1-4}$ haloalkyl, $C_{1-4}$ alkoxy, $C_{1-4}$ haloalkoxy, $C_{1-4}$ thioalkyl, or $C_{1-4}$ thiohaloalkyl;

$R^{13}$, $R^{14}$, $R^{15}$, $R^{16}$ and $R^{17}$ are each, independently, hydrogen, halogen, cyano, nitro, $C_{1-4}$ alkyl, C(O)CH$_3$, $C_{1-4}$ haloalkyl, $C_{1-4}$ alkoxy, $C_{1-4}$ haloalkoxy, $C_{1-4}$ thioalkyl, $C_{1-4}$ thiohaloalkyl, hydroxymethyl, or $C_{1-4}$ alkoxymethyl;

W is a single or a double bond;

Y is O, N($R^{18}$), S, or $(CR^{19}R^{20})(CR^{21}R^{22})_{m1}(CR^{23}R^{24})_{n1}$;

$R^{18}$ is hydrogen, $C_{1-4}$ alkyl, formyl, $C_{1-4}$ alkoxy($C_{1-4}$) alkyl, C(=O)$C_{1-4}$ alkyl, which may be substituted by halogen or $C_{1-4}$ alkoxy, or C(=O)O—$C_{1-6}$ alkyl, which may be substituted by halogen, $C_{1-4}$ alkoxy, or CN;

$R^{19}$, $R^{20}$, $R^{21}$, $R^{22}$, $R^{23}$ and $R^{24}$ are each independently hydrogen, halogen, hydroxy, $C_{1-4}$ alkoxy, $C_{1-6}$ alkyl, which may be substituted by 1 to 3 substituents selected from the group consisting of halogen, hydroxy, =O, $C_{1-4}$ alkoxy, O—C(O)—$C_{1-4}$ alkyl, phenyl, naphthyl, anthracyl, fluorenyl, indanyl, or a 3-7 membered carbocyclic ring which itself may be substituted by 1 to 3 methyl groups, $C_{1-6}$ alkenyl, which may be substituted by 1 to 3 substituents selected from the group consisting of halogen, hydroxy, =O, $C_{1-4}$ alkoxy, O—C(O)—$C_{1-4}$ alkyl, phenyl, naphthyl, anthracyl, fluorenyl, indanyl, or a 3-7 membered carbocyclic ring which itself may be substituted by 1 to 3 methyl groups, or a 3-7 membered carbocyclic ring, which may contain 1 heteroatom selected from the group consisting of nitrogen and oxygen, and wherein the 3-7 membered carbocyclic ring may be substituted by 1 to 3 methyl groups;

or $R^{19}$, $R^{20}$ together with the carbon atom to which they are attached form a carbonyl-group, a 3-5 membered carbocyclic ring, which may be substituted by 1 to 3 methyl groups, $C_{1-6}$ alkylidene, which may be substituted by 1 to 3 methyl groups, or $C_{3-6}$ cycloalkylidene, which may be substituted by 1 to 3 methyl groups;

$m_1$ is 0 or 1;

$n_1$ is 0 or 1;

$R^{13a}$ is a $C_1$-$C_4$ alkyl, $C_2$-$C_4$ alkenyl, or $C_2$-$C_4$ alkynyl group, which may be substituted by 1 to 6 substituents, each substituent independently selected from the group consisting of halogen, hydroxy, cyano, $C_{1-4}$ alkoxycarbonyl, formyl, nitro, $C_1$-$C_4$ alkoxy, $C_1$-$C_4$ haloalkoxy, $C_1$-$C_4$ alkylthio, $C_1$-$C_4$ haloalkylthio, HC(OR$^{29}$)=N—, and $R^{31}$OR$^{31}$NN=C(H)—;

$R^{29}$, $R^{30}$ and $R^{31}$, independently of one another, are hydrogen or $C_1$-$C_4$ alkyl;

$R^{13b}$ is a $C_1$-$C_6$ alkyl group, which may be substituted by 1 to 6 substituents, each substituent independently selected from the group consisting of halogen, hydroxy, cyano, $C_{1-4}$ alkoxycarbonyl, formyl, nitro, $C_1$-$C_4$ alkoxy, $C_1$-$C_4$ haloalkoxy, $C_1$-$C_4$ alkylthio, $C_1$-$C_4$ haloalkylthio, HC(OR$^{32}$)=N—, and $R^{33}R^{34}$NN=C(H)—;

$R^{32}$, $R^{33}$ and $R^{24}$, independently of one another, are hydrogen or $C_1$-$C_4$ alkyl;

$R^{13c}$ is hydrogen or halogen; and tautomers/isomers/enantiomers of these compounds;

said process comprising: reacting a compound of formula (II)

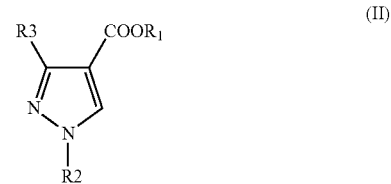

wherein

R1 is an organic residue, and

R2 and R3 are as defined above, with an amine of formula (III): QNHR4 (III) wherein Q is as defined above, in the presence of a base in a reaction medium which is essentially free of water.

2. The process according to claim 1, wherein the reaction medium contains not more than 1000 mg/kg of water.

3. A process for the manufacture of compounds of formula (I)

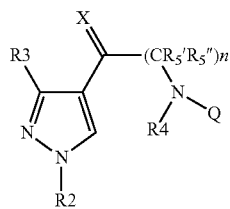
(I)

wherein
- R2 is H or an organic residue;
- R3 is H, an alkyl group having from 1 to 12 carbon atoms, a halogenated alkyl group having from 1 to 12 carbon atoms, an aralkyl group, an aryl group, or a halogen;
- R4 is H, an alkyl group having from 1 to 12 carbon atoms, a halogenated alkyl group having from 1 to 12 carbon atoms, an aralkyl group, an aryl group, or a halogen;
- R5' and R5" are each independently selected from the group consisting of H, an alkyl group having from 1 to 12 carbon atoms, a halogenated alkyl group having from 1 to 12 carbon atoms, an aralkyl group, an aryl group, and a halogen;
- n=0 to 10;
- X is oxygen or sulfur;
- Q is a group selected from the group consisting of formulae (Q1) to (Q38):

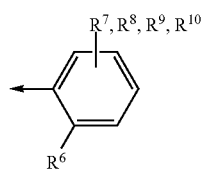
(Q1)

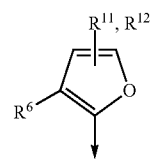
(Q2)

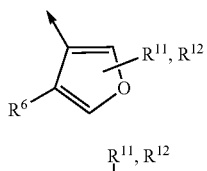
(Q3)

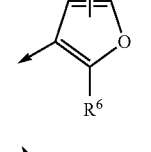
(Q4)

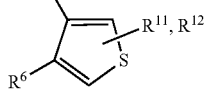
(Q5)

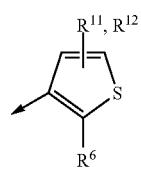
(Q6)

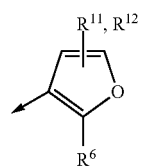
(Q7)

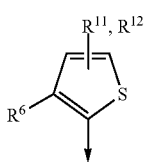
(Q8)

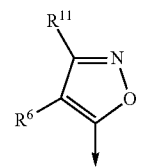
(Q9)

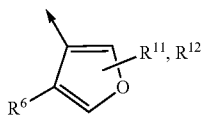
(Q10)

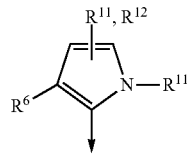
(Q11)

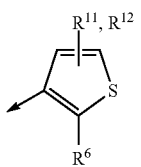
(Q12)

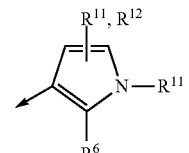
(Q13)

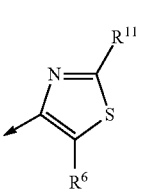
(Q14)

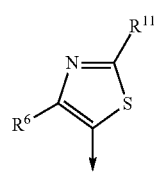 (Q15)
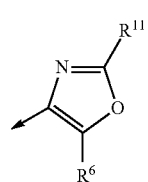 (Q16)
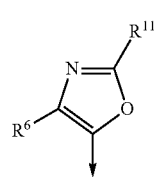 (Q17)
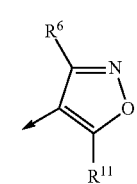 (Q18)
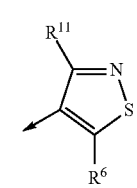 (Q19)
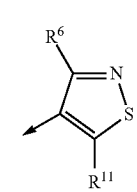 (Q20)
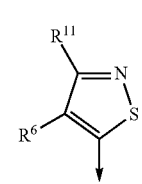 (Q21)
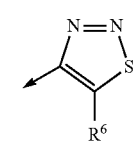 (Q22)
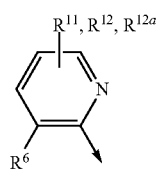 (Q23)
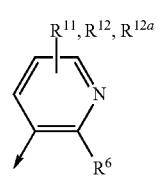 (Q24)
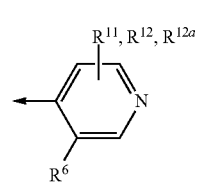 (Q25)
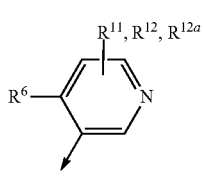 (Q26)
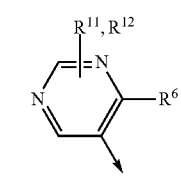 (Q27)
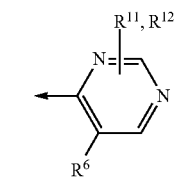 (Q28)
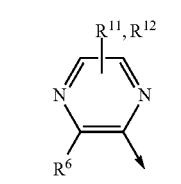 (Q29)
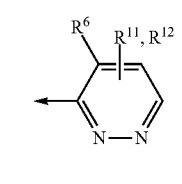 (Q30)
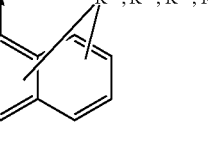 (Q31)
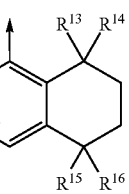 (Q32)

-continued

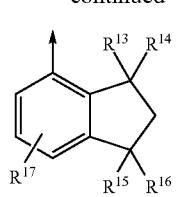
(Q33)

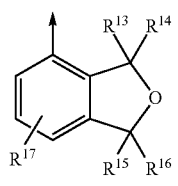
(Q34)

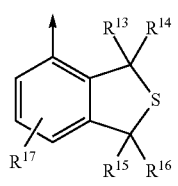
(Q35)

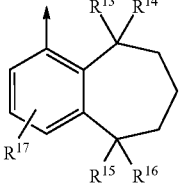
(Q36)

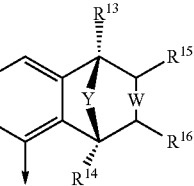
(Q37)

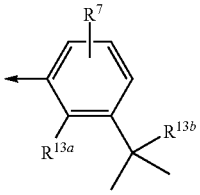
(Q38)

wherein:

$R^6$ is a hydrogen, $C_{1-12}$ alkyl, $C_{2-12}$ alkenyl, or $C_{2-12}$ alkynyl group, which may be substituted by 1 to 6 substituents, each substituent independently selected from the group consisting of halogen, cyano, $C_{1-4}$ alkoxy, $C_{1-4}$ thioalkyl, COO—$C_{1-4}$ alkyl, =N—OH, =N-0-($C_{1-4}$ alkyl), $C_{3-8}$ cycloalkyl, which may itself be substituted by 1 to 3 substituents, each independently selected from the group consisting of $C_{1-4}$ alkyl, halogen, $C_{1-4}$ alkoxy, and $C_{1-4}$ haloalkoxy, and $C_{4-8}$ cycloalkenyl, which may itself be substituted by 1 to 3 substituents, each independently selected from the group consisting of $C_{1-4}$ alkyl, halogen, $C_{1-4}$ alkoxy, and $C_{1-4}$ haloalkoxy;

or $R^6$ is a $C_{3-8}$ cycloalkyl, $C_{4-8}$ cycloalkenyl or $C_{5-8}$ cycloalkadienyl group, which may be substituted by 1 to 3 substituents, each independently selected from the group consisting of halogen, $C_{1-4}$ alkyl, $C_{1-4}$ haloalkyl, $C_{1-4}$ alkoxy, $C_{1-4}$ haloalkoxy, $C_{1-4}$ thioalkyl, $C_{3-6}$ cycloalkyl, which may itself be substituted by 1 to 3 substituents, each independently selected from the group consisting of $C_{1-4}$ alkyl, halogen, $C_{1-4}$ alkoxy, and $C_{1-4}$ haloalkoxy, and phenyl, which may itself be substituted by 1 to 5 independently selected halogen atoms;

or $R^6$ is a $C_{6-12}$ bicycloalkyl, $C_{6-12}$ bicycloalkenyl, or $C_{6-12}$ bicycloalkadienyl group, which may be substituted by 1 to 3 substituents, each independently selected from the group consisting of halogen, $C_{1-4}$ alkyl, and $C_{1-4}$ haloalkyl;

or $R^6$ is phenyl, which may be substituted by 1 to 3 substituents, each independently selected from the group consisting of halogen, cyano, nitro, $C_{1-4}$ alkyl, $C_{1-4}$ haloalkyl, $C_{1-4}$ alkoxy, $C_{1-4}$ alkylthio, $C_{1-4}$ haloalkoxy, $C_{1-4}$ haloalkylthio, C(H)=N—OH, C(H)=N—O($C_{1-6}$ alkyl), C($C_{1-6}$ alkyl)=N—OH, C($C_{1-6}$ alkyl)=N—O—($C_{1-6}$ alkyl), $(Z)C\equiv CR$, $(Z)_nCR^{28}=CR^{26}R^{27}$, phenyl, which may itself be substituted by 1 to 3 substituents, each independently selected from the group consisting of halogen, cyano, nitro, $C_{1-4}$ alkyl, $C_{1-4}$ haloalkyl, $C_{1-4}$ alkoxy, $C_{1-4}$ haloalkoxy, $C_{1-4}$ haloalkylthio, C(H)=N—OH, C(H)=N—O($C_{1-6}$ alkyl), C($C_{1-6}$ alkyl)=N—OH, and C($C_{1-6}$ alkyl)=N—O—($C_{1-6}$ alkyl), and thienyl, which may itself be substituted by 1 to 3 substituents, each independently selected from the group consisting of halogen, cyano, nitro, $C_{1-4}$ alkyl, $C_{1-4}$ haloalkyl, $C_{1-4}$ alkoxy, $C_{1-4}$ haloalkoxy, $C_{1-4}$ haloalkylthio, C(H)=N—OH, C(H)=N—O($C_{1-6}$ alkyl), C($C_{1-6}$ alkyl)=N—OH, and C($C_{1-6}$ alkyl)=N—O—($C_{1-6}$ alkyl);

or $R^6$ is a 5-6 membered heterocyclic ring, wherein the heterocyclic ring contains 1 to 3 heteroatoms, each heteroatom independently selected from the group consisting of oxygen, sulphur and nitrogen, wherein the heterocyclic ring may be substituted by 1 to 3 substituents, each independently selected from the group consisting of halogen, cyano, nitro, $C_{1-4}$ alkyl, $C_{1-4}$ haloalkyl, $C_{1-4}$ alkoxy, $C_{1-4}$ alkylthio, $C_{1-4}$ alkylthio, $C_{1-4}$ haloalkoxy, C(H)=N—O—($C_{1-6}$ alkyl) and C($C_{1-6}$ alkyl)=N—O—($C_{1-6}$ alkyl), $C_{2-5}$ alkenyl, $C_{2-5}$ alkynyl, CHO, COOC$_1$-C$_6$ alkyl, $C_1$-$C_4$ alkoxy-$C_1$-$C_4$ alkyl, $C_1$-$C_4$ haloalkoxy-$C_1$-$C_4$ alkyl, $(Z)_pC\equiv CR$, $(Z)_nCR^{28}=CR^{26}R^{27}$, phenyl, which may itself be substituted by 1 to 3 substituents, each independently selected from the group consisting of halogen, cyano, nitro, $C_{1-4}$ alkyl, $C_{1-4}$ haloalkyl, $C_{1-4}$ alkoxy, $C_{1-4}$ haloalkoxy, $C_{1-4}$ haloalkylthio, C(H)=N—OH, C(H)=N—O($C_{1-6}$ alkyl), C($C_{1-6}$ alkyl)=N—OH, and C($C_{1-6}$ alkyl)=N—O—($C_{1-6}$ alkyl), and thienyl, which may itself be substituted by 1 to 3 substituents, each independently selected from the group consisting of halogen, cyano, nitro, $C_{1-4}$ alkyl, $C_{1-4}$ haloalkyl, $C_{1-4}$ alkoxy, $C_{1-4}$ haloalkoxy, $C_{1-4}$ haloalkylthio, C(H)=N—OH, C(H)=N—O($C_{1-6}$ alkyl), C($C_{1-6}$ alkyl)=N—OH, and C($C_{1-6}$ alkyl)=N—O—($C_{1-6}$ alkyl), and wherein two substituents on adjacent carbon atoms of the 5-6 membered heterocyclic ring together may form a group —CR$^{6a}$—CR$^{6a}$=CR$^{6a}$—CR$^{6a}$—, wherein each R$^{6a}$ independently is selected from the group consisting of hydrogen, halogen, cyano, nitro, $C_{1-4}$ alkyl, $C_{1-4}$ haloalkyl, $C_{1-4}$ alkoxy, $C_{1-4}$ haloalkoxy, $C_{1-4}$ haloalkylthio, C(H)=N—OH, C(H)=N—O($C_{1-6}$ alkyl), C($C_{1-6}$ alkyl)=N—OH, and C($C_{1-6}$ alkyl)=N—O—($C_{1-6}$ alkyl);

or $R^6$ is an aliphatic saturated or unsaturated group containing 3 to 13 carbon atoms and at least one silicon atom, wherein the aliphatic group may contain 1 to 3 heteroatoms, each heteroatom independently selected from the group consisting of oxygen, nitrogen, and sulphur, and wherein the aliphatic group may be substituted by 1 to 4 independently selected halogen atoms;

or $R^6$ is $(CR^aR^b)_m$-Cy-$(CR^cR^d)_n$—$Y_1$;

or $R^6$ is $C_{1-6}$ alkoxy, $C_{1-6}$ haloalkoxy, $C_{2-6}$ alkenyloxy, $C_{2-6}$ haloalkenyloxy, $C_{2-6}$ alkinyloxy, $C_{3-6}$ cycloalkyloxy, $C_{1-4}$ alkyl-$C_{3-7}$ cycloalkyloxy, $C_{5-7}$ cycloalkenyloxy, or $C_{1-4}$ alkyl-$C_{5-7}$ cycloalkenyloxy;

Z is $C_{1-4}$ alkylene;

p is 0 or 1;

$R^{25}$ is hydrogen, halogen, $C_{1-4}$ alkyl, $C_{1-4}$ haloalkyl, $C_{1-4}$ alkoxy($C_{1-4}$) alkyl, $C_{1-4}$ haloalkoxy ($C_{1-4}$ alkyl, or Si($C_{1-4}$ alkyl)$_3$;

$R^{26}$ and $R^{27}$ are each, independently, hydrogen, halogen, $C_{1-4}$ alkyl, or $C_{1-4}$ haloalkyl;

$R^{25}$ is hydrogen, $C_{1-4}$ alkyl, or $C_{1-4}$ haloalkyl;

$R^a$, $R^b$, $R^c$ and $R^d$ are each, independently, hydrogen or a $C_{1-4}$ alkyl group, which may substituted by 1 to 6 substituents, each substituent independently selected from the group consisting of halogen, hydroxy, cyano, carboxyl, methoxycarbonyl, ethoxycarbonyl, methoxy, ethoxy, methylsulfonyl, ethylsulfonyl, difluoromethoxy, trifluoromethoxy, trifluoromethylthio, and trifluorothiomethoxy;

Cy is a carbocyclic or heterocyclic 3-7 membered ring, which may be saturated, unsaturated or aromatic and which may contain a silicon atom as a ring member, wherein $(CR^aR^b)_m$ and $(CR^cR^d)_n$ may be bound either to the same carbon or silicon atom of Cy or to different atoms separated by 1, 2 or 3 ring members, wherein the carbocyclic or heterocyclic 3-7 membered ring may be substituted by 1 to 6 substituents, each substituent independently selected from the group consisting of halogen, $C_{1-4}$ alkyl, $C_{2-4}$ alkenyl, $C_{1-4}$ haloalkyl, $C_{1-4}$ alkoxy, and halo-$C_{1-4}$ alkoxy;

$Y_1$ is $Si(O_{p_1}Z^1)(O_qZ^2)(O_sZ^3)$ and provided that Cy contains a silicon atom as a ring member then $Y_1$ may also be hydrogen;

$Z^1$ and $Z^2$ are independently methyl or ethyl;

$Z^3$ is a $C_{1-4}$ alkyl or a $C_{2-4}$ alkenyl group, which may be interrupted by one heteroatom selected from the group consisting of O, S, and N, and wherein the $C_{1-4}$ alkyl or $C_{2-4}$ alkenyl group may be substituted by 1 to 3 independently selected halogen atoms;

m and n are each independently 0, 1, 2 or 3;

$p_1$, q and s are each independently 0 or 1;

$R^7$, $R^8$, $R^9$, $R^{10}$, $R^{11}$, $R^{12}$ and $R^{12a}$ are each, independently, hydrogen, halogen, cyano, nitro, $C_{1-4}$ alkyl, $C_{1-4}$ haloalkyl, $C_{1-4}$ alkoxy, $C_{1-4}$ haloalkoxy, $C_{1-4}$ thioalkyl, or $C_{1-4}$ thiohaloalkyl;

$R^{13}$, $R^{14}$, $R^{15}$, $R^{16}$ and $R^{17}$ are each, independently, hydrogen, halogen, cyano, nitro, $C_{1-4}$ alkyl, $C(O)CH_3$, $C_{1-4}$ haloalkyl, $C_{1-4}$ alkoxy, $C_{1-4}$ haloalkoxy, $C_{1-4}$ thioalkyl, $C_{1-4}$ thiohaloalkyl, hydroxymethyl, or $C_{1-4}$ alkoxymethyl;

W is a single or a double bond;

Y is O, N($R^{18}$), S, or $(CR^{19}R^{20})(CR^{21}R^{22})_{m_1}(CR^{23}R^{24})_{n_1}$;

$R^{18}$ is hydrogen, $C_{1-4}$ alkyl, formyl, $C_{1-4}$ alkoxy($C_{1-4}$) alkyl, C(=O)$C_{1-4}$ alkyl, which may be substituted by halogen or $C_{1-4}$-alkoxy, or C(=O)O—$C_{1-6}$ alkyl, which may be substituted by halogen, $C_{1-4}$ alkoxy, or CN;

$R^{19}$, $R^{20}$, $R^{21}$, $R^{22}$, $R^{23}$ and $R^{24}$ are each independently hydrogen, halogen, hydroxy, $C_{1-4}$ alkoxy, $C_{1-6}$ alkyl, which may be substituted by 1 to 3 substituents selected from the group consisting of halogen, hydroxy, =O, $C_{1-4}$ alkoxy, O—C(O)—$C_{1-4}$ alkyl, phenyl, naphthyl, anthracyl, fluorenyl, indanyl or a 3-7 membered carbocyclic ring which itself may be substituted by 1 to 3 methyl groups, $C_{1-6}$ alkenyl, which may be substituted by 1 to 3 substituents selected from the group consisting of halogen, hydroxy, =O, $C_{1-4}$ alkoxy, O—C(O)—$C_{1-4}$ alkyl, phenyl, naphthyl, anthracyl, fluorenyl, indanyl or a 3-7 membered carbocyclic ring which itself may be substituted by 1 to 3 methyl groups, or a 3-7 membered carbocyclic ring, which may contain 1 heteroatom selected from the group consisting of nitrogen and oxygen, and wherein the 3-7 membered carbocyclic ring may be substituted by 1 to 3 methyl groups;

or $R^{19}$, $R^{20}$ together with the carbon atom to which they are attached form a carbonyl-group, a 3-5 membered carbocyclic ring, which may be substituted by 1 to 3 methyl groups, $C_{1-6}$ alkylidene, which may be substituted by 1 to 3 methyl groups, or $C_{3-6}$ cycloalkylidene, which may be substituted by 1 to 3 methyl groups;

$m_1$ is 0 or 1;

$n_1$ is 0 or 1;

$R^{13a}$ is a $C_1$-$C_4$ alkyl, $C_2$-$C_4$ alkenyl or $C_2$-$C_4$ alkynyl group, which may be substituted by 1 to 6 substituents, each substituent independently selected from the group consisting of halogen, hydroxy, cyano, $C_{1-4}$ alkoxycarbonyl, formyl, nitro, $C_1$-$C_4$ alkoxy, $C_1$-$C_4$ haloalkoxy, $C_1$-$C_4$ alkylthio, $C_1$-$C_4$ haloalkylthio, HC(OR$^{29}$)=N—, and R$^{30}$R$^{31}$NN=C(H)—;

$R^{29}$, $R^{30}$ and $R^{31}$, independently of one another, are hydrogen or $C_1$-$C_4$ alkyl;

$R^{13b}$ is a $C_1$-$C_6$ alkyl group, which may be substituted by 1 to 6 substituents, each substituent independently selected from the group consisting of halogen, hydroxy, cyano, $C_{1-4}$ alkoxycarbonyl, formyl, nitro, $C_1$-$C_4$ alkoxy, $C_1$-$C_4$ haloalkoxy, $C_1$-$C_4$ alkylthio, $C_1$-$C_4$ haloalkylthio, HC(OR$^{32}$)=N—, and R$^{33}$R$^{34}$NN=C(H)—;

$R^{32}$, $R^{33}$ and $R^{24}$ independently of one another are hydrogen or $C_1$-$C_4$ alkyl;

$R^{13c}$ is hydrogen or halogen; and tautomers/isomers/enantiomers of these compounds;

said process comprising: reacting a compound of formula (II)

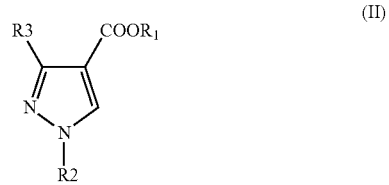

wherein
R1 is an organic residue, and
R2 and R3 are as defined above,
with an amine of formula (III): QNHR4 (III) wherein Q is as defined above, in the presence of a base which is used in an amount equal to or greater than 0.5 equivalents per mol of said amine of formula (III).

4. The process according to claim 1, wherein the base comprises a non-nucleophilic base selected from the group consisting of sterically hindered alcoholates, amines; lithium compounds; silicium compounds; and aluminium compounds.

5. The process according to claim 4, wherein the non-nucleophilic base is a sterically hindered alcoholates selected from the group consisting of potassium tert-butoxide and sodium tert-butoxide.

6. The process according to claim 1, wherein the reaction is carried out in an inert solvent selected from the group consisting of hydrocarbons, halogenated hydrocarbons, halogenated aromatic hydrocarbons, straight chain ethers, cyclic ethers, and nitriles.

7. The process according to claim 6, wherein the inert solvent is a cyclic ether.

8. The process according to claim 3, wherein R1 is selected from the group consisting of H, $C_1$-$C_8$-alkyl, $C_1$-$C_8$-haloalkyl $C_3$-$C_8$-cycloalkyl, $C_1$-$C_4$ alkoxy-$C_1$-$C_4$ alkyl, $C_3$-$C_8$ cycloalkoxy-$C_1$-$C_4$ alkyl, $C_2$-$C_8$ alkenyl, and benzyl optionally substituted by 1, 2, or 3 substituents $R^{Y1}$ independently of one another selected from the group consisting of $C_1$-$C_4$ alkyl, $C_1$-$C_4$ alkoxy, and nitro.

9. The process according to claim 3, wherein R2 is selected from the group consisting of H, $C_1$-$C_4$ alkyl, benzyl and phenyl, where benzyl and phenyl are optionally substituted by 1, 2, or 3 substituents $R^{Y2}$ independently of one another selected from the group consisting of halogen, nitrile, nitro, $C_1$-$C_4$-alkyl, $C_1$-$C_4$-haloalkyl, $C_1$-$C_4$-alkoxy, and $C_1$-$C_4$-haloalkoxy.

10. The process according to claim 3, wherein R3 is a fluorinated alkyl group selected from the group consisting of fluoromethyl, difluoromethyl, trifluoromethyl, chlorofluoromethyl, dichlorofluoromethyl, and chlorodifluoromethyl.

11. The process according to claim 3, wherein R4 is selected from the group consisting of H, $C_1$-$C_8$-alkyl, benzyl and phenyl.

12. The process according to claim 3, wherein Q is a group of formula Q1 or Q37.

13. The process according to claim 3, wherein the base comprises a non-nucleophilic base selected from the group consisting of sterically hindered alcoholates, amines, lithium compounds, silicium compounds, and aluminium compounds.

14. The process according to claim 13, wherein the non-nucleophilic base is a sterically hindered alcoholates selected from the group consisting of potassium tert-butoxide and sodium tert-butoxide.

15. The process according to claim 6 wherein the inert solvent is selected from the group consisting of straight chain ethers and cyclic ethers.

16. The process according claim 3, wherein the reaction is carried out in an inert solvent selected from the group consisting of hydrocarbons, halogenated hydrocarbons, halogenated aromatic hydrocarbons, straight chain ethers, cyclic ethers, and nitriles.

17. The process according to claim 3, wherein R1 is ethyl, wherein R2 is methyl, and wherein R3 is difluoromethyl.

18. A process for the manufacture of compounds of formula (I)

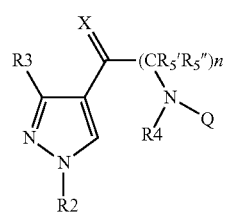

(I)

wherein
R2 is H or an organic residue;
R3 is H, an alkyl group having from 1 to 12 carbon atoms, a halogenated alkyl group having from 1 to 12 carbon atoms, an aralkyl group, an aryl group, or a halogen;
R4 is H, an alkyl group having from 1 to 12 carbon atoms, a halogenated alkyl group having from 1 to 12 carbon atoms, an aralkyl group, an aryl group, or a halogen;
R5' and R5" are each independently selected from the group consisting of H, an alkyl group having from 1 to 12 carbon atoms, a halogenated alkyl group having from 1 to 12 carbon atoms, an aralkyl group, an aryl group, and a halogen;
n=0 to 10;
X is oxygen or sulfur;
Q is a group selected from the group consisting of formulae (Q39) to (Q41):

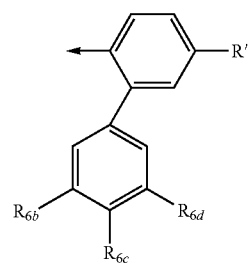

(Q39)

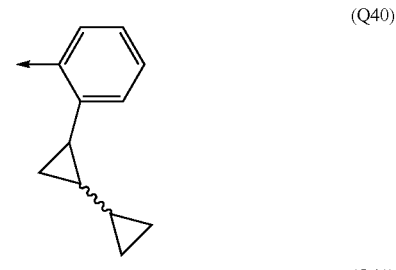

(Q40)

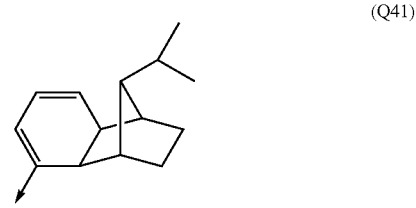

(Q41)

wherein R', $R_{6b}$, $R_{6c}$ and $R_{6d}$ are each, independently, hydrogen or halogen;

said process comprising: reacting a compound of formula (II)

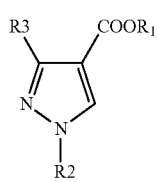

(II)

wherein
R1 is an organic residue, and
R2 and R3 are as defined above,
with an amine of formula (III): QNHR4 (III) wherein Q is as defined above, in the presence of a base which is used in an amount equal to or greater than 0.5 equivalents per mol of said amine of formula (III).

19. The process of claim 18, wherein R1 is ethyl, wherein R2 is methyl, and wherein R3 is difluoromethyl.

* * * * *